US007763772B2

(12) United States Patent
Bressan et al.

(10) Patent No.: US 7,763,772 B2
(45) Date of Patent: Jul. 27, 2010

(54) ACTIVATION OF THE ARABIDOPSIS HYPERTALL (HYT1/YUCCA6) LOCUS AFFECTS SEVERAL AUXIN MEDIATED RESPONSES

(75) Inventors: Ray A Bressan, West Lafayette, IN (US); Paul M Hasegawa, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 415 days.

(21) Appl. No.: 11/985,312

(22) Filed: Nov. 14, 2007

(65) Prior Publication Data

US 2008/0307542 A1 Dec. 11, 2008

Related U.S. Application Data

(60) Provisional application No. 60/858,855, filed on Nov. 14, 2006.

(51) Int. Cl.
*C12N 15/82* (2006.01)

(52) U.S. Cl. .......................... 800/278; 800/298; 435/458

(58) Field of Classification Search ........................ None
See application file for complete search history.

(56) References Cited

U.S. PATENT DOCUMENTS

| 4,407,956 A | 10/1983 | Howell |
| 4,945,050 A | 7/1990 | Sanford et al. |

FOREIGN PATENT DOCUMENTS

WO    WO 02/40689    5/2002

OTHER PUBLICATIONS

Blast results, Accession No. NP_197944, Aug. 21, 2009.*
Yamada et al., Database Embl. [online], "*Arabidopsis thaliana* unknown protein (At5g25620) mRNA, complete cds." XP-002487495, retrieved from EBI accession No. EMBL: AY065229 (Dec. 13, 2001)—2 pages.
Yamada et al., Database Accession No. AY065229, "Arabidopsis Full Length cDNA Clones", (Dec. 3, 2001)—3 pages.
Kim, J. I., A. Sharkhuu, J. B. Jin, P. Li, J. C. Jeong et al., "yucca6, a dominant mutation in Arabidopsis, affects auxin accumulation and auxin-related phenotypes." (Nov. 2007), Plant Physiol. 145: 722-735.
De La Bastide M., et al., Database Embl. [online], "*Arabidopsis thaliana* chromosome v map near 60.5 cM, complete sequence." XP-002487496, retrieved from EBI accession No. EMBL: AC006601 (Mar. 25, 1999)—3 pages.
Alonso JM, et al. (2003) Genome-Wide Insertional Mutagenesis of *Arabidopsis thaliana*. Science 301: 653-657.
Bak, S., et al. (2001) CYP83B1, a Cytochrome P450 at the Metabolic Branch Point in Auxin and Indole Glucosinolate Biosynthesis in Arabidopsis. Plant Cell 13:101-111.
Barlier, Isabelle, et al. (2000) The *SUR2* gene of *Arabidopsis thaliana* encodes the cytochrome P450 CYP83B1, a modulator of auxin homeostasis. Proc Natl Acad Sci USA 97: 14819-14824.
Blakeslee, JJ, et al. (2005) Auxin transport. Curr. Opin. Plant Biol 8: 1-7.
Boerjan, W., et al. (1995) *superroot*, a Recessive Mutation in Arabidopsis, Confers Auxin Overproduction. Plant Cell 7: 1405-1419.
Cheng, Youfa, et al. (2006) Auxin biosynthesis by the YUCCA flavin monooxygenases controls the formation of floral organs and vascular tissues in *Arabidopsis*. Genes Dev 20: 1790-1799.
Clough, SJ et al. (1998) Floral dip: a simplified method for *Agrobacterium*-mediated transformation of *Arabidopsis thaliana*. Plant J 16: 735-743.
Delarue, Marianne, et al. (1998) *Sur2* mutations of *Arabidopsis thaliana* define a new locus involved in the control of auxin homeostasis. Plant J 14: 603-611.
Dharmasiri, N. et al. (2005) The F-box protein TIR1 is an auxin receptor. Nature 435: 441-445.
Geisler, Markus, et al. (2005) Cellular efflux of auxin catalyzed by the Arabidopsis MDR/PGP transporter AtPGP1. Plant J. 44(2): 179-194.
Gong, Qingqiu, et al. (2005) Salinity stress adaptation competence in the extremophile *Thellungiella halophila* in comparison with its relative *Arabidopsis thaliana*. Plant J 44: 826-839.
Hellmann, Hanjo, et al. (2003) *Arabidopsis AXR6* encodes CUL1 implicating SCF E3 Ligases in auxin regulation of embryogenesis. EMBO J 22: 3314-3325.
Jin, Jing Bo, et al. (2003) The Arabidopsis Dynamin-Like Proteins ADL1 C and ADL1E Play a Critical Role in Mitochondrial Morphogenesis. Plant Cell 15: 2357-2369.
Jin, Jing Bo, et al. (2001) A New Dynamin-Like Protein, ADL6, Is Involved in Trafficking from the *trans*-Golgi Network to the Central Vacuole in Arabidopsis. Plant Cell 13: 1511-1525.
King, Joseph J., et al. (1995) A Mutation Altering Auxin Homeostasis and Plant Morphology in Arabidopsis. Plant Cell 7: 2023-2037.
Lee, Kwang Hee, et al. (2002) In vivo Import Experiments in Protoplasts Reveal the Importance of the Overall Context but Not Specific Amino Acid Residues of the Transit Peptide during Import into Chloroplasts. Mol Cells 14: 388-397.
Liu, C., et al. (1998) Tomato Phosphate Transporter Genes Are Differentially Regulated in Plant Tissues by Phosphorus. Plant Physiol 116: 91-99.
Liu, Yao-Guang, et al. (1995) Efficient isolation and mapping of *Arabidopsis thaliana* T-DNA insert junctions by thermal asymmetric interlaced PCR. Plant J 8: 457-463.
Ljung, Karin, et al. (2005) Sites and Regulation of Auxin Biosynthesis in Arabidopsis Roots. Plant Cell 17: 1090-1104.
Marsch-Martinez, Nayelli, et al. (2002) Activation Tagging Using the *En-I* Maize Transposon System in Arabidopsis. Plant Physiol 129: 1544-1556.

(Continued)

*Primary Examiner*—Eileen B O Hara
(74) *Attorney, Agent, or Firm*—Barnes & Thornburg LLP; Alice O. Martin

(57) ABSTRACT

The present invention provides nucleotide sequences and a corresponding amino acid sequence of auxin overproduction mutants. Also provided are methods to improve plant growth, development, differentiation, increased tolerance to drought and delayed senescence as well as plants with drought tolerance and delayed senescence.

10 Claims, 11 Drawing Sheets

OTHER PUBLICATIONS

Mikkelsen, Michael Dalgaard, et al. (2000) Cytochrome P450 CYP79B2 from *Arabidopsis* Catalyzes the Conversion of Tryptophan to Indole-3-acetaldoxime, a Precursor of Indole Glucosinolates and Indole-3-acetic Acid. J Biol Chem 275: 33712-33717.

Miura, Kenji (2005) The *Arabidopsis* SUMO E3 ligase SIZ1 controls phosphate deficiency responses. Proc Natl Acad Sci USA 102: 7760-7765.

Miyazaki, S., et al. (2004) Transcript expression profiles of *Arabidopsis thaliana* grown under controlled conditions and open-air elevated concentrations of $CO_2$ and of $O_3$. Field Crops Res 90: 47-59.

Normanly, Jennifer, et al. (1993) *Arabidopsis thaliana* auxotrophs reveal a tryptophan-independent biosynthetic pathway for indole-3-acetic acid. Proc Natl Acad Sci USA 90: 10355-10359.

Romano, Charles P., et al. (1993) Uncoupling Auxin and Ethylene Effects in Transgenic Tobacco and Arabidopsis Plants. Plant Cell 5: 181-189.

Rus, Ana, et al. (2001) AtHKT1 is a salt tolerance determinant that controls $Na^+$ entry into plant roots. Proc Natl Acad Sci USA 98: 14150-14155.

Smolen, Gromoslaw, et al. (2002) Arabidopsis, Cytochrome P450 *cyp83B1* Mutations Activate the Tryptophan Biosynthetic Pathway. Genetics 160: 323-332.

Tobeña-Santamaria, Rafael, et al. (2002) Floozy of petunia is a flavin mono-oxygenase-like protein required for the specification of leaf and flower architecture. Genes Dev 16: 753-763.

Ulmasov, Tim, et al. (1997) Aux/IAA Proteins Repress Expression of Reporter Genes Containing Natural and Highly Active Synthetic Auxin Response Elements. Plant Cell 9: 1963-1971.

Woodward, Andrew W. et al. (2005) Auxin: Regulation, Action, and Interaction. Ann Bot (Lond) 95: 707-735.

Woodward, Claire, et al. (2005) Interaction of Auxin and ERECTA in Elaborating Arabidopsis Inflorescence Architecture Revealed by the Activation Tagging of a New Member of the YUCCA Family Putative Flavin Monooxygenases. Plant Physiol 139: 192-203.

Yamamoto, Yuko, et al. (2007) Auxin Biosynthesis by the *YUCCA* Genes in Rice. Plant Physiol 143: 1362-1371.

Yang, Xiaoqing, et al. (2004) The IAA1 Protein is encoded by *AXR5* and is a substrate of $SCF^{TIR1}$. Plant J 40: 772-782.

Zhao, Yunde, et al. (2001) A Role for Flavin Monooxygenase-Like Enzymes in Auxin Biosynthesis. Science 291: 306-309.

Zhao, Yunde, et al. (2002) Trp-dependent auxin biosynthesis in *Arabidopsis*: involvement of cytochrome P450s CYP79B2 and CYP79B3. Genes Dev 16: 3100-3112.

Bak, Soren, et al. (2001) The Involvement of Two P450 Enzymes, CYP83B1 and CYP83A', in Auxin Homeostasis and Glucosinolate Biosynthesis. Plant Physiol 127: 108-118.

Bak, Soren, et al. (1998) The presence of CYP79 homologues in glucosinolate-producing plants shows evolutionary conservation of the enzymes in the conversion of amino acid to aldoxime in the biosynthesis of cyanogenic glucosides and glucosinolates. Plant Mol Biol 38: 725-734.

Davies PJ, (2004) Plant Hormones: Biosynthesis, Signal Transduction, Action! Ed 3. Kluwer Academic Publishers, Dordrecht, The Netherlands, pp. vii-ix, 1-6.

Estelle, Mark A., et al. (1987) Auxin-resistant mutants of *Arabidopsis thaliana* with an altered morphology. Mol Gen Genet 206: 200-206.

Jaakola, Laura, et al. (2001) Isolation of High Quality RNA from Bilberry (Vaccinium myrtillus L.) Fruit. Mol Biotechnol 19: 201-203.

Jefferson, Richard A., et al. (1987) GUS fushions: β-glucuronidase as a sensitive and versatile gene fusion marker in higher plants. EMBO J 6: 3901-3907.

Kepinski, Stefan, et al. (2005) The *Arabidopsis* F-box protein TIR1 is an auxin receptor. Nature 435: 446-451.

Ljung, Karin, et al. (2001) Biosynthesis, conjugation, catabolism and homeostasis of indole-3-acetic acid in *Arabidopsis thaliana*. Plant Mol Biol 50: 309-332.

Muday, Gloria K., et al. (2001) Polar auxin transport: controlling where and how much. Trends Plant Sci 6: 535-542.

Müller, A., et al. (1998) Indole-3-acetic acid is synthesized from L-trypotophan in roots of *Arabidopsis thaliana*. Planta 206: 362-369.

Müller, A., et al. (2000) Indolic constituents and indole-3-acetic acid biosynthesis in the wild-type and a tryptophan auxotroph mutant of *Arabidopsis thaliana*. Planta 211: 855-863.

Saeed, A.I., et al. (2003) TM4: A Free, Open-Source System for Microarray Data Management and Analysis. Biotechniques 34: 374-378.

Schmid, Markus, et al. (2005) A gene expression map of *Arabidopsis thaliana* development. Nat Genet 37: 501-506.

Hedge, P., et al. (2000) A Concise Guide to cDNA Microarray Analysis. Biotechniques 29: 548-562.

Sabatini, S., Beis, D., Wolkenfelt, H., Murfett, J., Guilfoyle, T., Malamy, J., Benfey, P., Leyser, O., Bechtold, N., Weisbeek P. and Scheres, B. (1999). An auxin-dependent distal organizer of pattern and polartity in the *Arabidopsis* root. Cell 99: 463-472.

Hooley, R. (1998) Auxin signaling: Homing in with targeted genetics. Plant Cell 10:1581-1583.

Bartel, Annual Review of Plant Physiology and Plant Molecular Biology, Jun. 1997, vol. 48, pp. 51-66.

Davies, P.J. (1995). The plant hormones: their nature, occur and functions. In Plant Hormones Physiology, Biochemistry and Molecular Biology, P.J. Davies, ed. (Dordrecht: Kluwer Academic Publishers), pp. 1-12.

Ivan L.W. Ingelbrecht et. al., The Plant Cell, vol. 1:671-680, 1989, Different 3' End Regions Strongly Influence the Level of Gene Expression in Plant Cells.

Okamuro, J.K. And Goldberg, R.B., vol. 15 (1989) Chapter 1, "Regulation of Plant Gene Expression: General Principles" in Stumpf, P.K. and Conn, E.E. Eds, *The Biochemistry of Plants: A comprehensive treatise*. Academic Press. pp. 1-82.

Thomas H, Howarth CJ (2000) Five ways to stay green. J. Exp. Bot. 51: 329-337.

Swarup, R., et al. (2003) Auxin Transport: The Fountain of Life in Plants? Dev Cell 5: Index, 824-826.

Deblaere R, Reynaerts A, Hofte H, Hernalsteens JP, Leemans J, and Van Montagu M (1987) Vectors for cloning in plant cells. *Meth Enzymol* 153:277-292.

Klein et al., 1987, "High velocity microprojectiles for delivering nucleic acids into living cells", *Nature* 327:70-73.

Weissbach & Weissbach, "Methods for Plant Molecular Biology," Academic Press, NY, Section VIII, pp. 421-446 (1988).

Grierson & Corey, 1988, Plant Molecular Biology, 2d Ed., Blackie, London, Ch. 7-9.

Horsch et al., Science, 227:1229-1231, 1985.

De Framond AJ, Barton KA, Chilton MD (1983) Mini-Ti: a new vector strategy for plant genetic engineering. Biotechnology (N Y) 5: 262-269.

Hoekema A, Hirsch PR, Hooykaas PJJ, Schilperoort RA (1983) A binary plant vector strategy based on separation of *vir*- and T-region of the *Agrobacterium tumefaciens* Ti-plasmid. Nature 303: 179-180.

Klee HJ, Horsch RB, Hinchee MA, Hein MB, Hoffman NL (1987) The effects of overproduction of two *Agrobacterium tumefaciens* T-DNA auxin biosynthetic gene products in transgenic petunia plants. Genes Dev 1: 86-96.

Kares, C., Prinsen, E., Van Onckelen, H. and Otten, L. (1990) IAA synthesis and root induction with *iaa* genes under heat shock promoter control. *Plant Mol. Biol.* 15, 225-236.

\* cited by examiner

SEQUENCE LISTING

<160> NUMBER OF SEQ ID NOS: 30

<210> SEQ ID NO 1
<211> LENGTH: 417
<212> TYPE: PRT
<213> ORGANISM: Arabidopsis thaliana

<400> SEQUENCE: 1

```
Met Asp Phe Cys Trp Lys Arg Glu Met Glu Gly Lys Leu Ala His Asp
1               5                   10                  15

His Arg Gly Met Thr Ser Pro Arg Arg Ile Cys Val Val Thr Gly Pro
            20                  25                  30

Val Ile Val Gly Ala Gly Pro Ser Gly Leu Ala Thr Ala Ala Cys Leu
        35                  40                  45

Lys Glu Arg Gly Ile Thr Ser Val Leu Leu Glu Arg Ser Asn Cys Ile
    50                  55                  60

Ala Ser Leu Trp Gln Leu Lys Thr Tyr Asp Arg Leu His Leu His Leu
65                  70                  75                  80

Pro Lys Gln Phe Cys Glu Leu Pro Ile Ile Pro Phe Pro Gly Asp Phe
                85                  90                  95

Pro Thr Tyr Pro Thr Lys Gln Gln Phe Ile Glu Tyr Leu Glu Asp Tyr
            100                 105                 110

Ala Arg Arg Phe Asp Ile Lys Pro Glu Phe Asn Gln Thr Val Glu Ser
        115                 120                 125

Ala Ala Phe Asp Glu Asn Leu Gly Met Trp Arg Val Thr Ser Val Gly
    130                 135                 140

Glu Glu Gly Thr Thr Glu Tyr Val Cys Arg Trp Leu Val Ala Ala Thr
145                 150                 155                 160

Gly Glu Asn Ala Glu Pro Val Val Pro Arg Phe Glu Gly Met Asp Lys
                165                 170                 175

Phe Ala Ala Ala Gly Val Val Lys His Thr Cys His Tyr Lys Thr Gly
            180                 185                 190

Gly Asp Phe Ala Gly Lys Arg Val Leu Val Val Gly Cys Gly Asn Ser
        195                 200                 205

Gly Met Glu Val Cys Leu Asp Leu Cys Asn Phe Gly Ala Gln Pro Ser
    210                 215                 220

Leu Val Val Arg Asp Ala Val His Val Leu Pro Arg Glu Met Leu Gly
225                 230                 235                 240

Thr Ser Thr Phe Gly Leu Ser Met Phe Leu Leu Lys Trp Leu Pro Ile
                245                 250                 255

Arg Leu Val Asp Arg Phe Leu Leu Val Val Ser Arg Phe Ile Leu Gly
            260                 265                 270

Asp Thr Thr Leu Leu Gly Leu Asn Arg Pro Arg Leu Gly Pro Leu Glu
        275                 280                 285
```

```
Leu Lys Asn Ile Ser Gly Lys Thr Pro Val Leu Asp Val Gly Thr Leu
        290                 295                 300

Ala Lys Ile Lys Thr Gly Asp Ile Lys Val Cys Ser Gly Ile Arg Arg
305                 310                 315                 320

Leu Lys Arg His Glu Val Glu Phe Asp Asn Gly Lys Thr Glu Arg Phe
                325                 330                 335

Asp Ala Ile Ile Leu Ala Thr Gly Tyr Lys Ser Asn Val Pro Ser Trp
                340                 345                 350

Leu Lys Glu Asn Lys Met Phe Ser Lys Asp Gly Phe Pro Ile Gln
            355                 360                 365

Glu Phe Pro Glu Gly Trp Arg Gly Glu Cys Gly Leu Tyr Ala Val Gly
        370                 375                 380

Phe Thr Lys Arg Gly Ile Ser Gly Ala Ser Met Asp Ala Lys Arg Ile
385                 390                 395                 400

Ala Glu Asp Ile His Lys Cys Trp Lys Gln Asp Glu Gln Val Lys Lys
                405                 410                 415

Ile
```

```
<210> SEQ ID NO 2
<211> LENGTH: 1254
<212> TYPE: DNA
<213> ORGANISM: Arabidopsis thaliana

<400> SEQUENCE: 2
atggatttct gttggaagag agagatggaa ggtaaactag cacatgacca ccgcggcatg      60
acgtcaccgc gtcgtatctg cgtcgtcacc ggtccggtga tcgtaggcgc cggaccgtcg     120
ggactagcca cggcagcatg tttaaaagag agaggtatca cgtccgtact actagagaga     180
tcaaactgta tagcatcact atggcagctc aagacttatg accgtcttca tcttcaccct     240
cctaaacaat tctgtgaact tccgattata cccttccccg agatttccc tacctacccg      300 acgaagcaac agttcatcga gtaccttgag gactacgctc ggaggtttga cataaagccg     360
gagtttaacc aaacggttga gtcggctgcg tttgatgaaa accttgggat gtggcgcgtg     420
actagcgtgg gagaagaagg cacgacggag tatgtttgtc ggtggttagt ggcggcgacg     480
ggggagaatg cggagccggt ggtacctagg tttgagggga tggataagtt tgcagccgcc     540
ggggtagtta agcacacgtg tcattataaa accggtggag atttcgccgg aaaaagggtt     600
cttgtcgtcg gatgtggaaa ctccggtatg gaggtttgtt tggatctctg caacttcggt     660
gctcagcctt ctctcgttgt cagagacgct gtgcacgtcc taccacgaga gatgttgggt     720
acttcaactt tgggctgtc catgttctta ctgaaatggc tgcccatccg gcttgttgac      780
cgtttccttt tggttgtttc ccggttcatc ctcggggata ctacccttt aggtcttaac       840 aggccccggt taggtccact cgagctcaaa aatatctccg gtaaaactcc ggttctcgac     900
gttggcacgc tagccaaaat caaaaccgga gacattaagg tgtgttcggg ataagaagg      960 ttaaaacgac atgaagttga gttcgataac ggaaaaacag agagatttga cgccattata    1020
ttagcaactg gctacaaaag caacgtaccc tcttggctaa aggagaataa aatgtttagt    1080
aagaaagatg gatttccaat acaagagttc cctgagggat ggagagggga atgtgggcta    1140
tacgcggtcg gattcacaaa acgtgggatt agtggagcat caatggatgc aaagagaata    1200
gctgaagaca tacacaagtg ttggaaacaa gacgagcaag taaaaaaaat ctga          1254
```

<210> SEQ ID NO 3

```
<211> LENGTH: 2107
<212> TYPE: DNA
<213> ORGANISM: Arabidopsis thaliana

<400> SEQUENCE: 3
tccggtttac actctcatca aaacacaaac acaacgctta tctctctcac tctctttact        60
cattcttctc atttggataa gatctctctc tttctctccc tccttttcag cagattcaat       120
ccaaaccta acctctttga ttccgatctt tagagaatat ttctcttcaa aaatccatt        180
ataaatactt ttacttaact aaaactttt ttttaccat ctctcttttt tttttactt         240
actccatatg ccatcaatgt caaattgttc tttctgtcct tgttcttaa ttagtgtcac       300
caccaccacc actacttcta tactacaaac ccttctcgta ttctcttaac caatacgtac      360
ttattacacc aaaagtctct ttctctctat atatatag ataacagcca agagagagaa        420
ccaagaagaa gttatttct tgatggattt ctgttggaag agagagatgg aaggtaaact      480
agcacatgac caccgcggca tgacgtcacc gcgtcgtatc tgcgtcgtca ccggtccggt      540
gatcgtaggc gccggaccgt cgggactagc cacggcagca tgtttaaaag agagaggtat      600
cacgtccgta ctactagaga gatcaaactg tatagcatca ctatggcagc tcaagactta      660
tgaccgtctt catcttcacc ttcctaaaca attctgtgaa cttccgatta taccttccc      720
cggagatttc cctacctacc cgacgaagca acagttcatc gagtaccttg aggactacgc      780
tcggaggttt gacataaagc cggagtttaa ccaaacggtt gagtcggctg cgtttgatga      840
aaaccttggg atgtggcgcg tgactagcgt gggagaagaa ggcacgacgg agtatgtttg      900
tcggtggtta gtggcggcga cggggagaa tgcggagccg gtggtaccta ggtttgaggg       960
gatggataag tttgcagccg ccggggtagt taagcacacg tgtcattata aaaccggtgg     1020
agatttcgcc ggaaaaaggg ttcttgtcgt cggatgtgga aactccggta tggaggtttg     1080
tttggatctc tgcaacttcg gtgctcagcc ttctctcgtt gtcagagacg ctgtgcacgt     1140
cctaccacga gagatgttgg gtacttcaac ttttgggctg tccatgttct tactgaaatg     1200
gctgcccatc cggcttgttg accgtttcct tttggttgtt cccggttca tcctcgggga     1260
tactaccctt ttaggtctta acaggccccg gttaggtcca ctcgagctca aaaatatctc     1320
cggtaaaact ccggttctcg acgttggcac gctagccaaa atcaaaaccg gagacattaa     1380
ggtgtgttcg gggataagaa ggttaaaacg acatgaagtt gagttcgata acggaaaaac     1440
agagagattt gacgccatta tattagcaac tggctacaaa agcaacgtac cctcttggct     1500
aaaggagaat aaaatgttta gtaagaaaga tggatttcca atacaagagt tccctgaggg     1560
atggagaggg gaatgtgggc tatacgcggt cggattcaca aaacgtggga ttagtggagc     1620
atcaatggat gcaaagagaa tagctgaaga catacacaag tgttggaaac aagacgagca     1680
agtaaaaaaa atctgaatca aaacttattg actagacagt agagaaaagc taaggttttc     1740
tatcaagaaa acataacttg ccaaatgccg gtagcgatcg aaaaaaaatt gatggttttg     1800
tttcaaagga ggtgatgtaa attaagactt atctccagct gcaatgcaaa ttggggaaaa     1860
gaatgaaaag gaaatttagt gagagtgatt gtggtgggaa ttgatgatca tctgccccaa     1920
aggagaggag gggaccctct tctctttgca tgcttataac ccactttgta aatctttcta     1980
tacctttcttt ctatgttct aattttcctt ttctctttt ctttctttta ttttttgtttt      2040
tttagatttc catagttagg tatgctcttt gttttctttc tcttttttgg ttcaattttt     2100
tttggca                                                              2107
```

<210> SEQ ID NO 4
<211> LENGTH: 3558
<212> TYPE: DNA
<213> ORGANISM: Arabidopsis thaliana

<400> SEQUENCE: 4

| | | | | | | |
|---|---|---|---|---|---|---|
| tccggtttac | actctcatca | aaacacaaac | acaacgctta | tctctctcac | tctctttact | 60 |
| cattcttctc | atttggataa | gatctctctc | tttctctccc | tccttttcag | cagattcaat | 120 |
| ccaaacccta | acctctttga | ttccgatctt | tagagaatat | ttctcttcaa | aaaatccatt | 180 |
| ataaatactt | ttacttaact | aaaacttttt | tttttaccat | ctctcttttt | tttttttactt | 240 |
| actccatatg | ccatcaatgt | caaattgttc | tttctgtcct | ttgttcttaa | ttagtgtcac | 300 |
| caccaccacc | actacttcta | tactacaaac | ccttctcgta | ttctcttaac | caatacgtac | 360 |
| ttattacacc | aaaagtctct | ttctctctat | atatatatag | ataacagcca | agagagagaa | 420 |
| ccaagaagaa | gttatttttct | tgatggattt | ctgttggaag | agagagatgg | aaggtaaact | 480 |
| agcacatgac | caccgcggca | tgacgtcacc | gcgtcgtatc | tgcgtcgtca | ccggtccggt | 540 |
| gatcgtaggc | gccggaccgt | cgggactagc | cacggcagca | tgtttaaaag | agagaggtat | 600 |
| cacgtccgta | ctactagaga | gatcaaactg | tatagcatca | ctatggcagc | tcaagactta | 660 |
| tgaccgtctt | catcttcacc | ttcctaaaca | attctgtgaa | cttccgatta | tacccttccc | 720 |
| cggagatttc | cctacctacc | cgacgaagca | acagttcatc | gagtaccttg | aggactacgc | 780 |
| tcggaggttt | gacataaagc | cggagtttaa | ccaaacggtt | gagtcggctg | cgtttgatga | 840 |
| aaaccttggg | atgtggcgcg | tgactagcgt | gggagaagaa | ggcacgacgg | agtatgtttg | 900 |
| tcggtggtta | gtggcggcga | cggggggagaa | tgcggagccg | gtggtaccta | ggtttgaggg | 960 |
| gatggataag | tttgcagccg | ccgggggtagt | taagcacacg | tgtcattata | aaaccggtgg | 1020 |
| agatttcgcc | ggaaaaaggg | ttcttgtcgt | cggatgtgga | aactccggta | tggaggtttg | 1080 |
| tttggatctc | tgcaacttcg | gtgctcagcc | ttctctcgtt | gtcagagacg | ctgtgagttt | 1140 |
| cttttttttt | tttttttttt | tgcttttttcg | gtttcttgat | ttttttaaaa | tagaaagtat | 1200 |
| tgtggagatt | atattatcct | tttctcatgc | gttttcgata | ttttttgctcc | ttcatgtttt | 1260 |
| atggcttcta | ttgctaaaaa | acaaaatctt | gaaaagcttt | ttcattcaag | ttgatcttct | 1320 |
| gattgttttt | ctattcttaa | ctcaaagata | ttacctactt | ttttacaaac | ttttgctttt | 1380 |
| tgttttctag | attttttagaa | ttttcaggat | tatgtgtgta | ttctaagtat | tatccgatca | 1440 |
| atataataga | ttcataattc | atttaatagt | ataagcttgt | actaaattct | gttccacaaa | 1500 |
| tatgttttaa | gaggttcttt | tttttacagc | gctttaagat | gttctcgtta | aaagagtttt | 1560 |
| agaagaaaaa | aacttcatgt | ttaatattat | ggaaaatatt | acttgattaa | atgaacactc | 1620 |
| atattttga | agaaaatata | tataatataa | ttatatgcat | agcttaaaga | ttttttttttt | 1680 |
| actgttatcg | ataaaaagtg | attttttagat | ttcattgtta | caaaaaaaaa | agatttcatt | 1740 |
| gttacaaaat | tcttaaggaa | accaaattat | atacaaatat | atctagacta | atattgatct | 1800 |
| tctttggaag | tttaattacc | attctttatt | aattggctga | taatttcaga | gaaataatct | 1860 |
| gcacaaatat | tttccaattt | tttgccttta | cagtaattct | tttaaaagta | tcaaaatttc | 1920 |
| ttttgctttt | tcagtttgat | attcttatta | tttaatctgt | ttagaaaatt | caaaatttac | 1980 |
| gggaaaatac | aaaggctggt | attatcctaa | tttaagattt | tattccgtct | tttaggccct | 2040 |
| tgtgacttca | agttccaaca | atttgttaat | atagttttta | tatgaataaa | gaggtttacc | 2100 |
| taatttcttt | aatacataaa | tattattttt | ataacatttt | caaagaataa | aaactaagag | 2160 |

```
aacaacaact ttattgggat tgtcacgagc acgcgcaaac attctcacaa aagaaaagaa    2220
aaacagtctc ttaatattat tattcatgat aaactaatag ataataatat gattttctca    2280
tccaaattat ttatctgctg tattgctaat tatgttttct ttttacttgt gaaggtgcac    2340
gtcctaccac gagagatgtt gggtacttca acttttgggc tgtccatgtt cttactgaaa    2400
tggctgccca tccggcttgt tgaccgtttc cttttggttg tttcccggtt catcctcggg    2460
gatactaccc ttttaggtct taacaggccc cggttaggtc cactcgagct caaaaatatc    2520
tccggtaaaa ctccggttct cgacgttggc acgctagcca aaatcaaaac cggagacatt    2580
aaggtagtgt ataatctaat caaagaatat atgatatgaa tacatactaa aaaccagttt    2640
actgattgtg atagttgatt ttgttaatgg taaaaggtg tgttcgggga taagaaggtt     2700
aaaacgacat gaagttgagt tcgataacgg aaaaacagag agatttgacg ccattatatt    2760
agcaactggc tacaaaagca acgtaccctc ttggctaaag gtattcaata ataatgataa    2820
tattgttatt ttacctttgt ccaccttctt taacaaatta ttaaagtctt tattcttatt    2880
ttcttaagac caaaatata catccattat gaattttgta ctaaatgggt ttttggaaaa     2940
catataattt ttcaggagaa taaaatgttt agtaagaaag atggatttcc aatacaagag    3000
ttccctgagg gatggagagg ggaatgtggg ctatacgcgg tcggattcac aaaacgtggg    3060
attagtggag catcaatgga tgcaaagaga atagctgaag acatacacaa gtgttggaaa    3120
caagacgagc aagtaaaaaa aatctgaatc aaaacttatt gactagacag tagagaaaag    3180
ctaaggtttt ctatcaagaa aacataactt gccaaatgcc ggtagcgatc gaaaaaaaat    3240
tgatggtttt gtttcaaagg aggtgatgta aattaagact tatctccagc tgcaatgcaa    3300
attggggaaa agaatgaaaa ggaaatttag tgagagtgat tgtggtggga attgatgatc    3360
atctgcccca aaggagagga ggggaccctc ttctctttgc atgcttataa cccactttgt    3420
aaatctttct ataccttctt tctatgtttc taattttttct ttttctcttt tctttctttt   3480 attttttgttt tttagattt ccatagttag gtatgctctt tgtttttctt ctctttttg     3540 gttcaatttt ttttggca                                                  3558
```

<210> SEQ ID NO 5
<211> LENGTH: 18
<212> TYPE: DNA
<213> ORGANISM: Artificial
<220> FEATURE:
<223> OTHER INFORMATION: Artificial Primer

<400> SEQUENCE: 5
tggtactaat tcagcaat                                                  18

<210> SEQ ID NO 6
<211> LENGTH: 18
<212> TYPE: DNA
<213> ORGANISM: Artificial
<220> FEATURE:
<223> OTHER INFORMATION: Artificial Primer

<400> SEQUENCE: 6
actctacgta cattgaag                                                  18

<210> SEQ ID NO 7
<211> LENGTH: 20
<212> TYPE: DNA
<213> ORGANISM: Artificial
<220> FEATURE:
<223> OTHER INFORMATION: Artificial Primer

```
<400> SEQUENCE: 7
atgtgctttc aagttgtacg                                              20

<210> SEQ ID NO 8
<211> LENGTH: 20
<212> TYPE: DNA
<213> ORGANISM: Artificial
<220> FEATURE:
<223> OTHER INFORMATION: Artificial Primer

<400> SEQUENCE: 8
tttatctttc cttgcatggc                                              20

<210> SEQ ID NO 9
<211> LENGTH: 20
<212> TYPE: DNA
<213> ORGANISM: Artificial
<220> FEATURE:
<223> OTHER INFORMATION: Artificial Primer

<400> SEQUENCE: 9
gcatgtgctt tcaagttacg                                              20

<210> SEQ ID NO 10
<211> LENGTH: 20
<212> TYPE: DNA
<213> ORGANISM: Artificial
<220> FEATURE:
<223> OTHER INFORMATION: Artificial Primer

<400> SEQUENCE: 10
tttatctttc cttgcatggc                                              20

<210> SEQ ID NO 11
<211> LENGTH: 21
<212> TYPE: DNA
<213> ORGANISM: Artificial
<220> FEATURE:
<223> OTHER INFORMATION: Artificial Primer

<400> SEQUENCE: 11
gtatgcagcc attggttgat c                                            21

<210> SEQ ID NO 12
<211> LENGTH: 21
<212> TYPE: DNA
<213> ORGANISM: Artificial
<220> FEATURE:
<223> OTHER INFORMATION: Artificial Primer

<400> SEQUENCE: 12
cggtcataag tcttgagctg c                                            21

<210> SEQ ID NO 13
<211> LENGTH: 22
<212> TYPE: DNA
<213> ORGANISM: Artificial
<220> FEATURE:
<223> OTHER INFORMATION: Artificial Primer

<400> SEQUENCE: 13
tggttcacgt agtgggccat cg                                           22

<210> SEQ ID NO 14
```

```
<211> LENGTH: 24
<212> TYPE: DNA
<213> ORGANISM: Artificial
<220> FEATURE:
<223> OTHER INFORMATION: Artificial Primer

<400> SEQUENCE: 14
atggatttct gttggaagag agag                                          24

<210> SEQ ID NO 15
<211> LENGTH: 25
<212> TYPE: DNA
<213> ORGANISM: Artificial
<220> FEATURE:
<223> OTHER INFORMATION: Artificial Primer

<400> SEQUENCE: 15
tcagattttt tttacttgct cgtct                                         25

<210> SEQ ID NO 16
<211> LENGTH: 20
<212> TYPE: DNA
<213> ORGANISM: Artificial
<220> FEATURE:
<223> OTHER INFORMATION: Artificial Primer

<400> SEQUENCE: 16
atacaaagag gtacagcgag                                               20

<210> SEQ ID NO 17
<211> LENGTH: 18
<212> TYPE: DNA
<213> ORGANISM: Artificial
<220> FEATURE:
<223> OTHER INFORMATION: Artificial Primer

<400> SEQUENCE: 17
ttcttaggca tagcggcg                                                 18

<210> SEQ ID NO 18
<211> LENGTH: 21
<212> TYPE: DNA
<213> ORGANISM: Artificial
<220> FEATURE:
<223> OTHER INFORMATION: Artificial Primer

<400> SEQUENCE: 18
cggacaaaac cgatgaggtt g                                             21

<210> SEQ ID NO 19
<211> LENGTH: 21
<212> TYPE: DNA
<213> ORGANISM: Artificial
<220> FEATURE:
<223> OTHER INFORMATION: Artificial Primer

<400> SEQUENCE: 19
actcccccat tgcttgtgac c                                             21

<210> SEQ ID NO 20
<211> LENGTH: 24
<212> TYPE: DNA
<213> ORGANISM: Artificial
<220> FEATURE:
<223> OTHER INFORMATION: Artificial Primer

<400> SEQUENCE: 20
```

```
gcattgagtc ggataaaacc gatg                                         24

<210> SEQ ID NO 21
<211> LENGTH: 22
<212> TYPE: DNA
<213> ORGANISM: Artificial
<220> FEATURE:
<223> OTHER INFORMATION: Artificial Primer

<400> SEQUENCE: 21
tcaacgacga cgttctggtg ac                                           22

<210> SEQ ID NO 22
<211> LENGTH: 24
<212> TYPE: DNA
<213> ORGANISM: Artificial
<220> FEATURE:
<223> OTHER INFORMATION: Artificial Primer

<400> SEQUENCE: 22
atggaagtca ccaatgggct taac                                         24

<210> SEQ ID NO 23
<211> LENGTH: 25
<212> TYPE: DNA
<213> ORGANISM: Artificial
<220> FEATURE:
<223> OTHER INFORMATION: Artificial Primer

<400> SEQUENCE: 23
cataaggcag taggagcttc ggatc                                        25

<210> SEQ ID NO 24
<211> LENGTH: 28
<212> TYPE: DNA
<213> ORGANISM: Artificial
<220> FEATURE:
<223> OTHER INFORMATION: Artificial Primer

<400> SEQUENCE: 24
ctctagaatg gatttctgtt ggaagaga                                     28

<210> SEQ ID NO 25
<211> LENGTH: 28
<212> TYPE: DNA
<213> ORGANISM: Artificial
<220> FEATURE:
<223> OTHER INFORMATION: Artificial Primer

<400> SEQUENCE: 25
cctgcagtca gatttttttt acttgatc                                     28

<210> SEQ ID NO 26
<211> LENGTH: 29
<212> TYPE: DNA
<213> ORGANISM: Artificial
<220> FEATURE:
<223> OTHER INFORMATION: Artificial Primer

<400> SEQUENCE: 26
cggaattcat ggatttctgt tggaagaga                                    29

<210> SEQ ID NO 27
<211> LENGTH: 32
<212> TYPE: DNA
```

```
<213> ORGANISM: Artificial
<220> FEATURE:
<223> OTHER INFORMATION: Artificial Primer

<400> SEQUENCE: 27
ccaagctttc agatttttt tacttgctcg tc                                       32

<210> SEQ ID NO 28
<211> LENGTH: 28
<212> TYPE: DNA
<213> ORGANISM: Artificial
<220> FEATURE:
<223> OTHER INFORMATION: Artificial Primer

<400> SEQUENCE: 28
ctctagaatg gatttctgtt ggaagaga                                           28

<210> SEQ ID NO 29
<211> LENGTH: 28
<212> TYPE: DNA
<213> ORGANISM: Artificial
<220> FEATURE:
<223> OTHER INFORMATION: Artificial Primer

<400> SEQUENCE: 29
cggatccaga ttttttac ttgctcgt                                             28

<210> SEQ ID NO 30
<211> LENGTH: 28
<212> TYPE: DNA
<213> ORGANISM: Artificial
<220> FEATURE:
<223> OTHER INFORMATION: Artificial Primer

<400> SEQUENCE: 30
cggatcctca gatttttttt acttgctc                                           28
```

ACTIVATION OF THE ARABIDOPSIS HYPERTALL (HYT1/YUCCA6) LOCUS AFFECTS SEVERAL AUXIN MEDIATED RESPONSES

CROSS REFERENCE TO RELATED APPLICATIONS

This application claims priority under 35 U.S.C. §119 from U.S. Application Ser. No. 60/858,855 filed Nov. 14, 2006, which is incorporated herein in its entirety by reference.

ACKNOWLEDGEMENT OF FEDERAL RESEARCH SUPPORT

This invention was made, at least in part, with government support under grant no. 0350439-MCB awarded by the National Science Foundation. Accordingly, the United States government has certain rights in this invention.

REFERENCE TO SEQUENCE LISTING

The present application incorporates by reference a file named 1499P-012 Bressan sequences.ST25.txt including SEQ ID NO:1 to SEQ ID NO:30, provided in a computer readable form and filed with the present application. The sequence listing recorded on the CD-ROM is identical to the written (on paper) sequence listing provided herein.

BACKGROUND OF THE INVENTION

The present invention relates to yucca6-1D, the peptide/protein YUCCA6 and methods for increasing plant growth, development and differentiation by introducing YUCCA6 into a plant. All publications cited in this application are herein incorporated by reference.

Auxin is an essential plant hormone that influences many aspects of plant growth and development including cell division and elongation, differentiation, tropisms, apical dominance, senescence, abscission and flowering (Hooley, Plant Cell (1998) 10:1581-4). Not only is auxin a plant growth regulator, it is also likely to be a morphogen (Sabatini et al., Cell (1999) 99:463-472). Although auxin has been studied for more than 100 years, its biosynthesis, transport, and signaling pathways remain elusive. In order to understand the biological functions of auxin, it is necessary to elucidate how auxin is synthesized, transported, and used as a signaling agent.

Indole-3-acetic acid (IAA), the first auxin to be chemically identified, appears to be the major endogenous auxin (Davies, The Plant Hormones: Their Nature, Occurrence, and Functions (1995) Kluwer Academic Publishers, 1-12). Based on its structural similarities, tryptophan has been proposed as the auxin biosynthesis precursor (Bartel, Ann Rev Plant Physiol (1997) 48:51-66). Many pathways have been proposed for converting tryptophan to IAA, but at present, none has been proven. Tryptophan can be converted to indole-pyruvate by transferring the amino group. Indole-pyruvate can be further converted to indole-acetaldehyde, which can be oxidized to IAA. Tryptamine, a decarboxylated product of tryptophan, has been proposed as an auxin biosynthesis intermediate.

Auxins are crucial for plant viability and development. Numerous physiological studies indicate that the major naturally occurring auxin, Indole-3-acetic acid (IAA) functions in a plethora of important aspects of plant development and growth, including apical dominance, tropic responses to light and gravity, root and shoot architecture, vascular differentiation, embryo patterning and shoot elongation (Davies, 2004).

Changes in endogenous auxin levels induce genes such as SMALL AUXIN-UP RNAs (SAURs), GH3-related transcripts and AUXIN/INDOLE-3-ACETIC ACID (Aux/IAA) family members via the TIR1/AFB receptor mechanism (Dharmasiri et al., 2005; Kepinski and Leyser, 2005). The movement of auxin throughout the plant, especially by polar transport mechanisms, has been the interest of classical and current studies aimed at understanding the function of this important hormone. The quantitative temporal and spatial distributions of IAA in a plant are crucial to accomplish proper growth and development (Swarup et al., 2003; Muday et al., 2001; Blakeslee et al., 2005). Although IAA pools in a plant could be maintained at appropriate levels via auxin biosynthesis, conjugation, degradation, and transport mechanisms, de novo biosynthesis is the primal step to achieve the crucial level of auxin. However the understanding of auxin biosynthesis is still incomplete.

Analytical and feeding studies have described in detail where IAA and related compounds accumulate (Lijung et al., 2001, 2005), but application of these techniques to screens of loss-of-function mutants have not yielded enough information to fully characterize overlapping IAA biosynthetic pathways. Other efforts to dissect these pathways in *Arabidopsis* (*Arabidopsis thaliana*) have focused on isolation of mutants that are resistant to exogenously applied auxins. This approach has been highly successful for the identification of auxin receptors and elucidation of auxin signaling pathways (Estelle and Somerville, 1987; Hellman et al., 2003; Yang et al., 2004), but has contributed less to elucidating IAA biosynthetic pathways.

A more productive avenue of research has been the identification and characterization of loss-of-function mutants exhibiting altered growth phenotypes. Auxin overproduction mutants such as supperroot1 (sur1) and supperroot2 (sur2) have been identified and characterized from *Arabidopsis*. These mutants were isolated from loss-of-function screening, because the loss of their functions attenuates depletion of auxin levels (Bak et al., 1998, 2001; Mikkelsen et al., 2000), indicating that gene products involved directly in auxin biosynthesis may be redundant.

Recently, application of a gain-of-function approach, activation tagging, in *Arabidopsis* has led to breakthroughs in the study of IAA biosynthesis. In independent efforts, activation tagging revealed five loci in *Arabidopsis* that encode proteins affecting auxin biosynthesis (Zhao et al., 2001; Marsch-Martinez et al., 2002; Woodward et al., 2005). These loci have been categorized into the YUCCA family of flavin monooxygenase (FMO)-like proteins. This family includes 11 members in the *Arabidopsis* genome (Zhao et al., 2001; Cheng et al., 2006). Activation-tagged yucca mutants exhibit signature phenotypes found in auxin overproduction mutants such as sur1 and sur2, and transgenic plants that overexpress the *Agrobacterium tumefaciens* phytohormone-biosynthetic gene iaaM (Zhao et al., 2001; Marsch-Martinez et al., 2002; Woodward et al., 2005). Double, triple, and quadruple mutants of YUCCA family members display dramatic developmental defects that are rescued by the bacterial auxin biosynthesis gene iaaM. This reverse genetic study along with previous work by Zhao et al. (2001) has revealed not only the functional redundancy but also some functional and physiological specificities among YUCCA members. Furthermore, the involvement of YUCCA in auxin biosynthesis has also been shown in rice (*Oryza sativa*) and petunia (*Petunia hybrida*; Tobeña-Santamaria et al., 2002; Yamamoto et al., 2007). Although it is clear that the YUCCA genes play critical roles in maintaining auxin levels in plants, the cellular and biochemical characteristics and specific functions of each family member have not been fully elucidated. In addition, although YUCCA1 recombinant protein was reported to have enzymatic activity, no reports of catalytic functions of other YUCCA proteins have appeared.

The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

The invention includes a method for increasing YUCCA6 levels in a plant by introducing YUCCA6 into a plant producing yucca6-1D and yucca6-2D and growing the plant. Methods for manipulating auxin biosysnthesis and/or the growth of a plant include introducing YUCCA6 into the plant and growing the plant under conditions whereby the drought tolerance of the plant is increased, senescence is delayed, plant growth is enhanced, plant size is increased, and/or growth rate is enhanced.

Embodiments of the invention include a plant produced by the method of the invention, including plant tissue, seeds, and other plant cells or parts derived from the plant containing yucca6 and/or 35S:YUCCA6.

A preferred embodiment of the invention relates to a method for producing a drought tolerant plant comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce drought tolerance.

In a further embodiment of the present invention provides a method for producing a drought tolerant plant comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce drought tolerance, wherein the nucleotide sequence is the sequence of SEQ ID NO:2.

Another embodiment of the present invention further provides a method for producing a drought tolerant plant comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce drought tolerance, wherein the nucleotide sequence is the sequence of SEQ ID NO:3.

Yet another embodiment of the present invention provides a method for producing a drought tolerant plant comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce drought tolerance, wherein the nucleotide sequence is the sequence of SEQ ID NO:4.

One embodiment of the present invention provides a method for producing a drought tolerant plant comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce drought tolerance, wherein the nucleotide sequence is the genomic sequence containing a T-DNA insertion upstream of the start codon.

Still another embodiment of the present invention provides a method for producing a drought tolerant plant comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce drought tolerance, wherein the nucleotide sequence is the genomic sequence containing a T-DNA insertion, wherein the T-DNA insertion is in the 5' untranslated region.

Another embodiment of the present invention further provides a method for producing a drought tolerant plant comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce drought tolerance, wherein the nucleotide sequence is the genomic sequence containing a T-DNA insertion, wherein the T-DNA insertion is about 10 kb upstream of the start codon.

Yet another embodiment of the present invention provides a method for producing a drought tolerant plant comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce drought tolerance, wherein the said plant is *Arabidopisis thaliana*.

In another aspect of the invention the YUCCA6 locus which is a complement of nucleotide sequence 8923112 to 8950669 of GenBank Accession Number NC_003076 is herein incorporated by reference.

One embodiment of the present invention provides a method for producing a plant with delayed senescence comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce delayed senescence.

Another embodiment of the present invention provides a method for producing a plant with delayed senescence comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce delayed senescence, wherein the nucleotide sequence is the sequence of SEQ ID NO: 2.

Still another embodiment of the present invention provides a method for producing a plant with delayed senescence comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce delayed senescence, wherein the nucleotide sequence is the sequence of SEQ ID NO:3.

Yet another embodiment of the present invention provides a method for producing a plant with delayed senescence comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce delayed senescence, wherein the nucleotide sequence is the sequence of SEQ ID NO:4.

Still another embodiment of the present invention provides a method for producing a plant with delayed senescence comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce delayed senescence, wherein the nucleotide sequence is the genomic sequence containing a T-DNA insertion, wherein the T-DNA insertion is upstream of the start codon.

A further embodiment of the present invention provides a method for producing a plant with delayed senescence comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce delayed senescence, wherein the nucleotide sequence is the genomic sequence containing a T-DNA insertion, wherein the T-DNA insertion is in the 5' untranslated region.

Another embodiment of the present invention provides a method for producing a plant with delayed senescence comprising stably transforming a plant with an expression vector comprising a nucleotide sequence encoding a flavin-containing monooxygenase having the amino acid sequence of SEQ ID NO:1, isolating a stably transformed plant containing the nucleotide sequence, wherein the nucleotide sequence when expressed in a plant will induce delayed senescence, wherein the nucleotide sequence is the genomic sequence containing a T-DNA insertion, wherein the T-DNA insertion is about 10 kb upstream of the start codon.

In an additional embodiment of the present invention provides a method for producing a plant with delayed senescence comprising stably transforming a plant with an expression vector comprising a nucleotide sequence encoding a flavin-containing monooxygenase having the amino acid sequence of SEQ ID NO. 1, isolating a stably transformed plant containing the nucleotide sequence, wherein the nucleotide sequence when expressed in a plant will induce delayed senescence, wherein said plant is *Arabidopisis thaliana*.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

In FIG. 1A, sos3-1 wild-type plant (left) and sos3-1 yucca6-1D plant (right) were grown on soil for 8 weeks. In FIG. 1B, 20-week old sos3-1 wild-type (left) and sos3-1 yucca6-1D plants are shown. In FIG. 1C, 20-week old transgenic plants with only the vector ($Pro_{35S}$, left) and with $Pro_{35S}$:YUCCA6 (right) are shown.

FIG. 2A illustrates the gene organization of HYT1 (YUCCA6) and schematic representation of T-DNA insertion alleles. Arrow boxes indicate predicted genes near T-DNA insertion position. LTR is long terminal repeat sequence. Boxes represent exons, and the intervening lines denote introns. The location of T-DNA insertion alleles of hyt1-1D (yucca6-1D) and hyt1-2D (yucca6-2D) are shown as boxes above the genomic structures. T-DNA inserts with dark gray boxes (35S enhancers) denote the activation-tagged alleles. Overexpression construct for ORF (open-reading frame) is shown below the genomic region of HYT1 (YUCCA6). NOS indicates nopaline synthase. In FIG. 2B HYT1 (YUCCA6) gene expressions in hyt1-1D (yucca6-1D) and hyt1-2D (yucca6-2D) are compared with wild type. Total RNA was extracted from 4-week-old mature rosette leaves of wild-type and mutants. ACTIN was used for internal standard.

FIG. 3A shows hyt1-D (yucca6-1D) and hyt1-2D (yucca6-2D) mutant seedlings with their wild type plants, Col-0gl1 and Col-0 respectively, grown for 7 days and 14 days on MS medium or 25 days on soil. FIG. 3B shows wild type and hyt1-1D (yucca6-1D) and hyt1-2D (yucca6-2D) plants grown on MS media for 4 days in light (left) and dark (right) conditions. FIG. 3C shows the hypocotyle length of hyt1-1D (yucca6-1D) and hyt1-2D (yucca6-2D) seedlings grown for 10 days on MS media containing 0.8% in agar compared with their wild-types. FIG. 3D shows 6-week-old mature plants of wild-type and hyt1-1D (yucca6-1D), scale bar is 2 cm. FIG. 3E shows roots of wild-type and hyt1-1D (yucca6-1D) plants grown in hydroponic culture condition for 3 weeks. Soil grown 3-week-old seedlings were transferred to the hydroponic solution. FIG. 3F shows flowers of wild-type and the hyt1-1D (yucca6-1D) plants. FIG. 3G shows the cauline leaf of 2-month-old wild-type and hyt1-1D plant (yucca6-1D). FIG. 3H shows the seeds of wild-type (left) and hyt1-1D (yucca6-1D) (right) plants before (above) and after imbibing water.

In FIG. 4A wild-type and yucca6-1D, 3.5-week old soil grown plants were grown under water deficiency (drought conditions) and well-watered conditions (control) for 12 days. The photographs of the plants were taken 2-days after re-watering. In FIG. 4B yucca6-2D and wild-type plants were grown under water deficiency (drought) conditions for 10 days and photographed 2 days after re-watering. In FIG. 4C a transgenic plant with 35S:

YUCCA6 and a plant with the vector alone were grown under water deficiency (drought) conditions for 10 days and photographed 2 days after re-watering.

Figure 5:
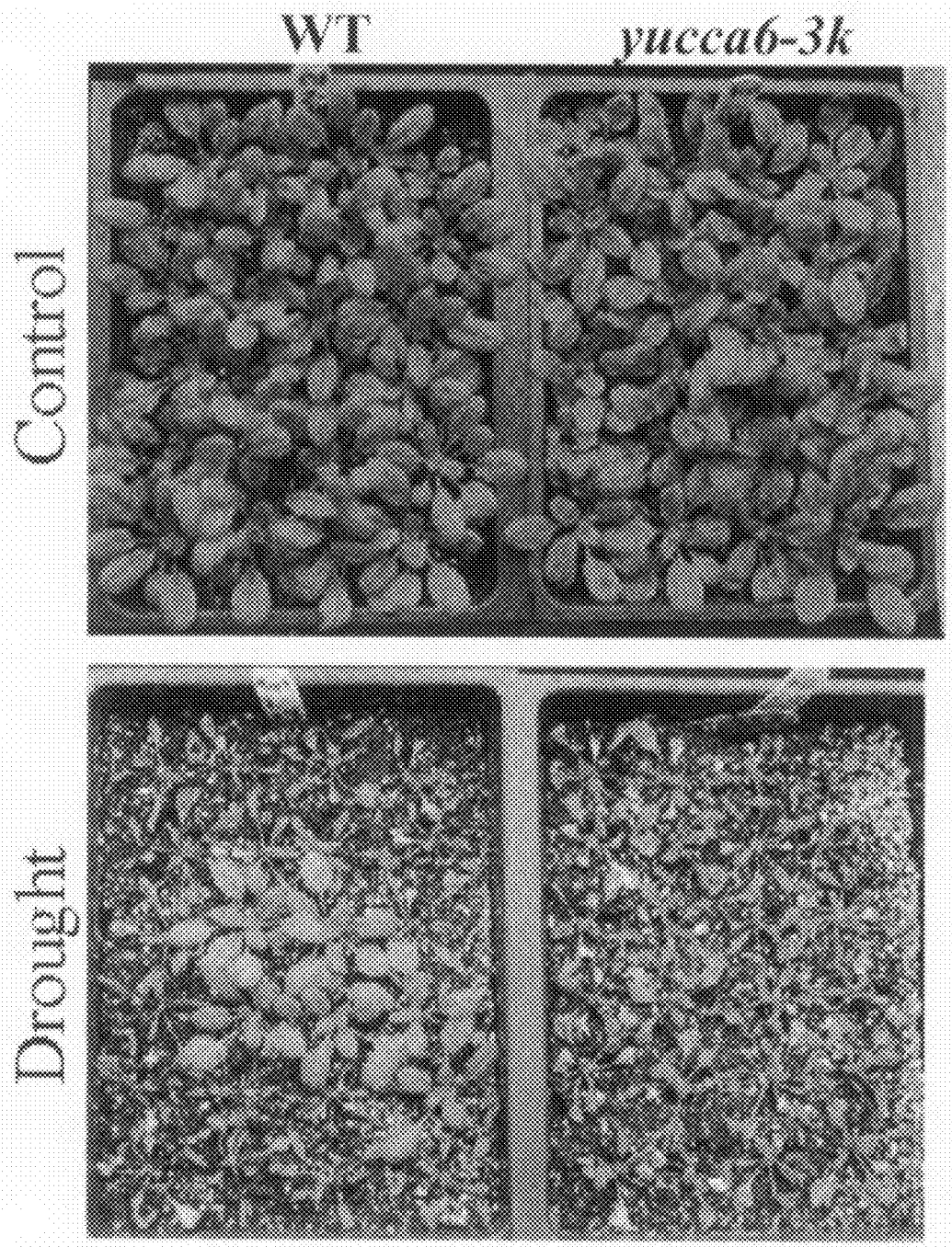

FIG. 5 shows that a knock-out of YUCCA6 causes sensitivity to drought stress. Wild-type and yucca6-3k (knock-out mutant) 3-week old soil grown plants were grown under water deficiency (drought) conditions and well-watered conditions (control) for 12 days. Photographs were taken 2 days after re-watering.

Figure 6:
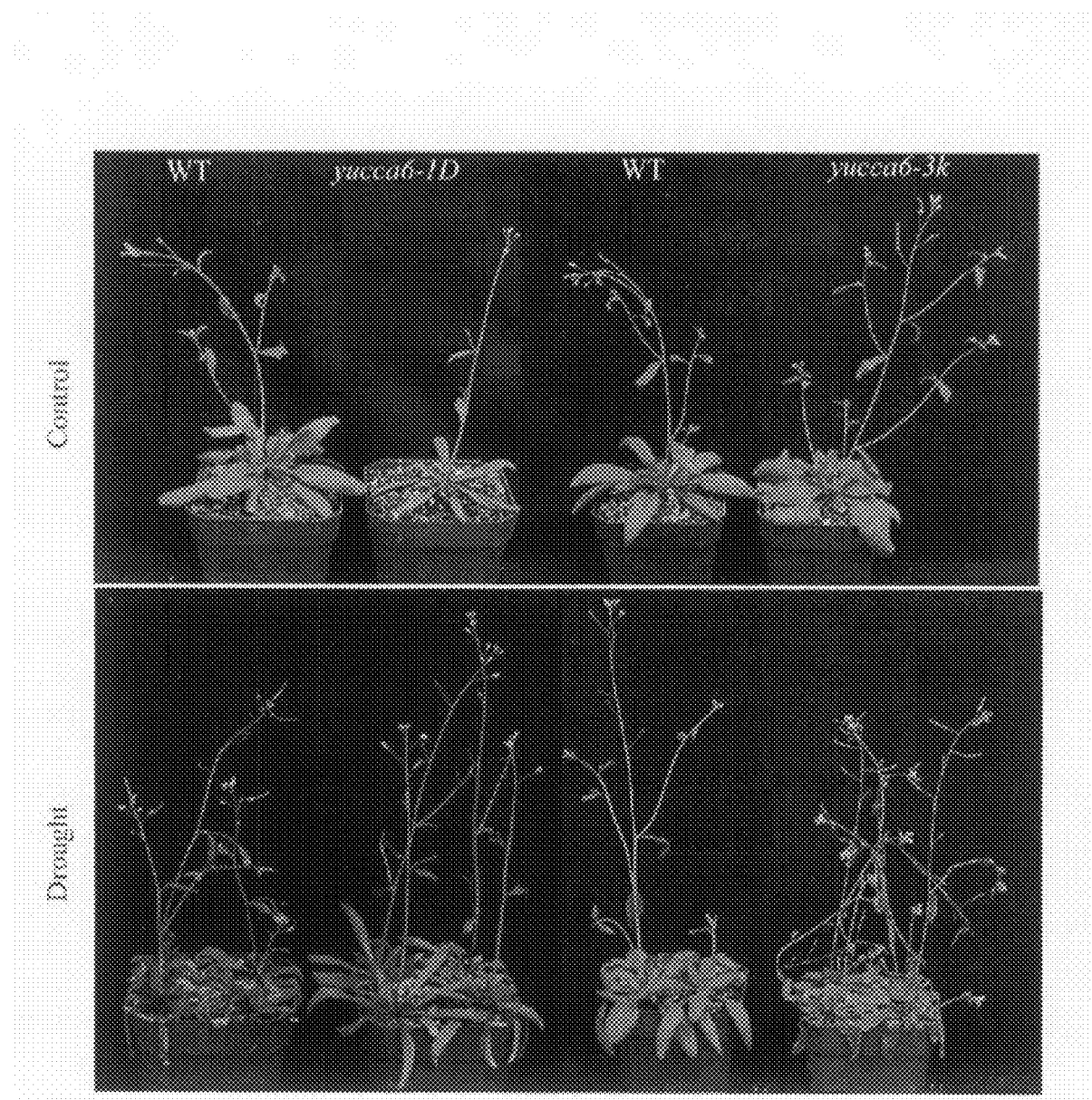

FIG. 6 shows wilting phenotypes observed during drought stress. Wild-type, yucca6-1D (overexpression mutant) and yucca6-3k (knock-out mutant) were grown under water deficiency (drought) conditions and well-watered conditions (control) for 12 days. Photographs were taken before re-watering.

FIGS. 7A-7D shows the delayed senescence phenotype of yucca6-1D mutant. FIG. 7A is of a 20-week old soil grown yucca6-1D plant. FIGS. 7B, 7C and 7D show close-up views of FIG. 7A showing that the 20-week old yucca6-1D plant still has flowers and new branches.

Figure 8:
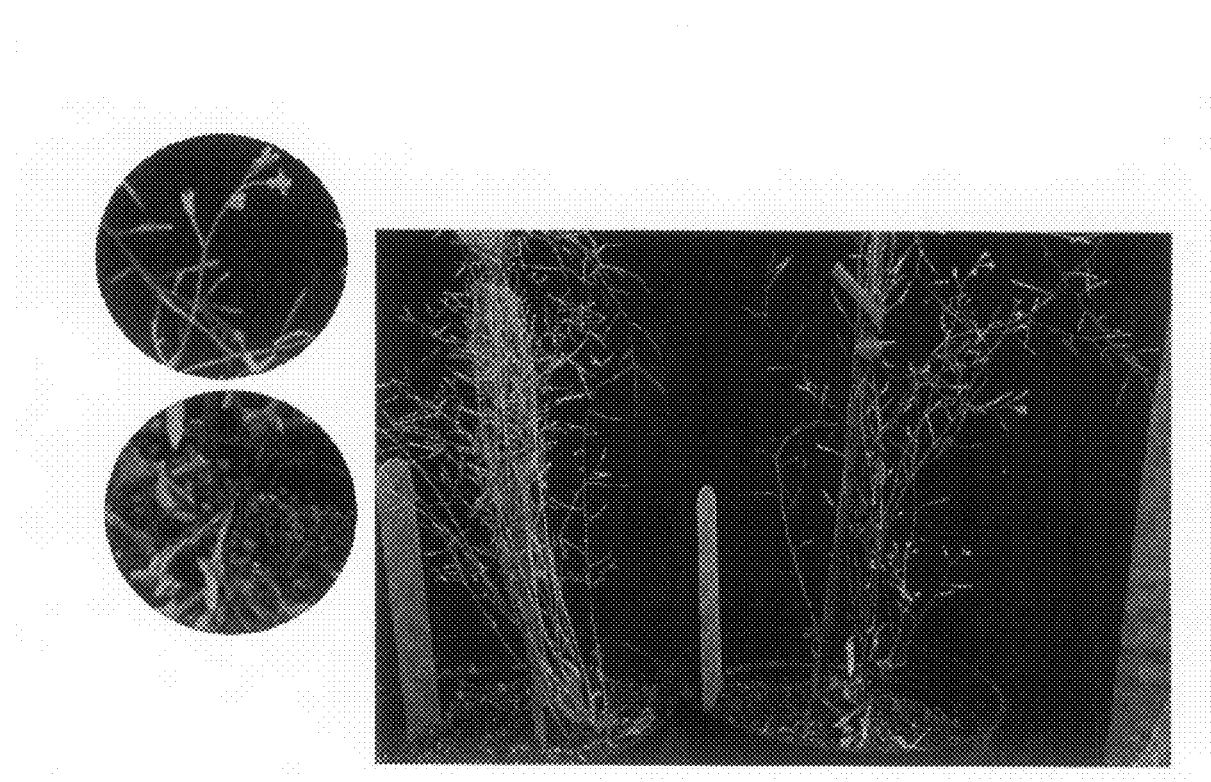

FIG. 8 shows the delayed senescence phenotype of a transgenic plant having 35S:YUCCA6. 20-week old soil grown transgenic plants having only the vector (left side of large panel) or having 35S:YUCCA6 (right side of large panel) are shown. Insets are close-ups of the branches and flowers of both plants.

Figure 9:
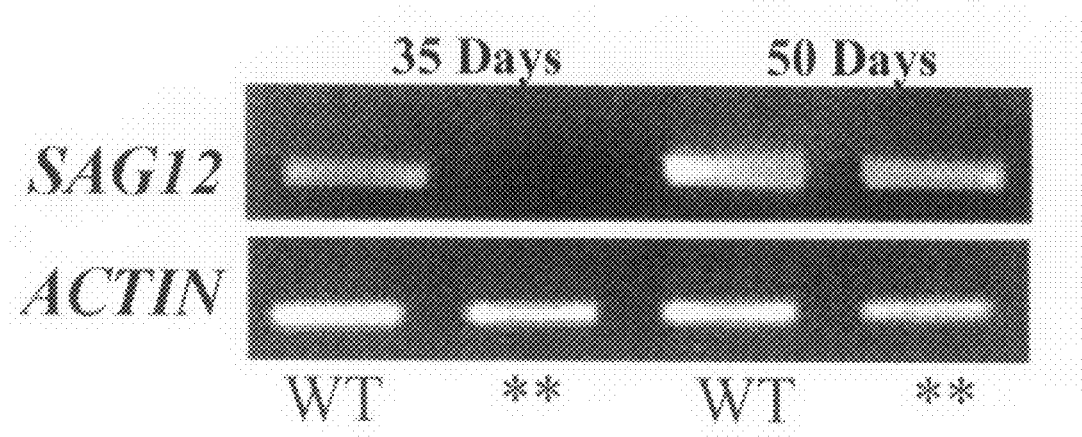

FIG. 9 shows expression of the SAG12 (Senescence Associated Gene 12) transcript in wild-type and yucca6-1D mutant. SAG12 expression levels were detected by RT-PCR. RNA was extracted from 35 day-old and 50 day-old soil grown wild-type and yucca6-1D plants. Actin was used as a loading control.

Figure 10:
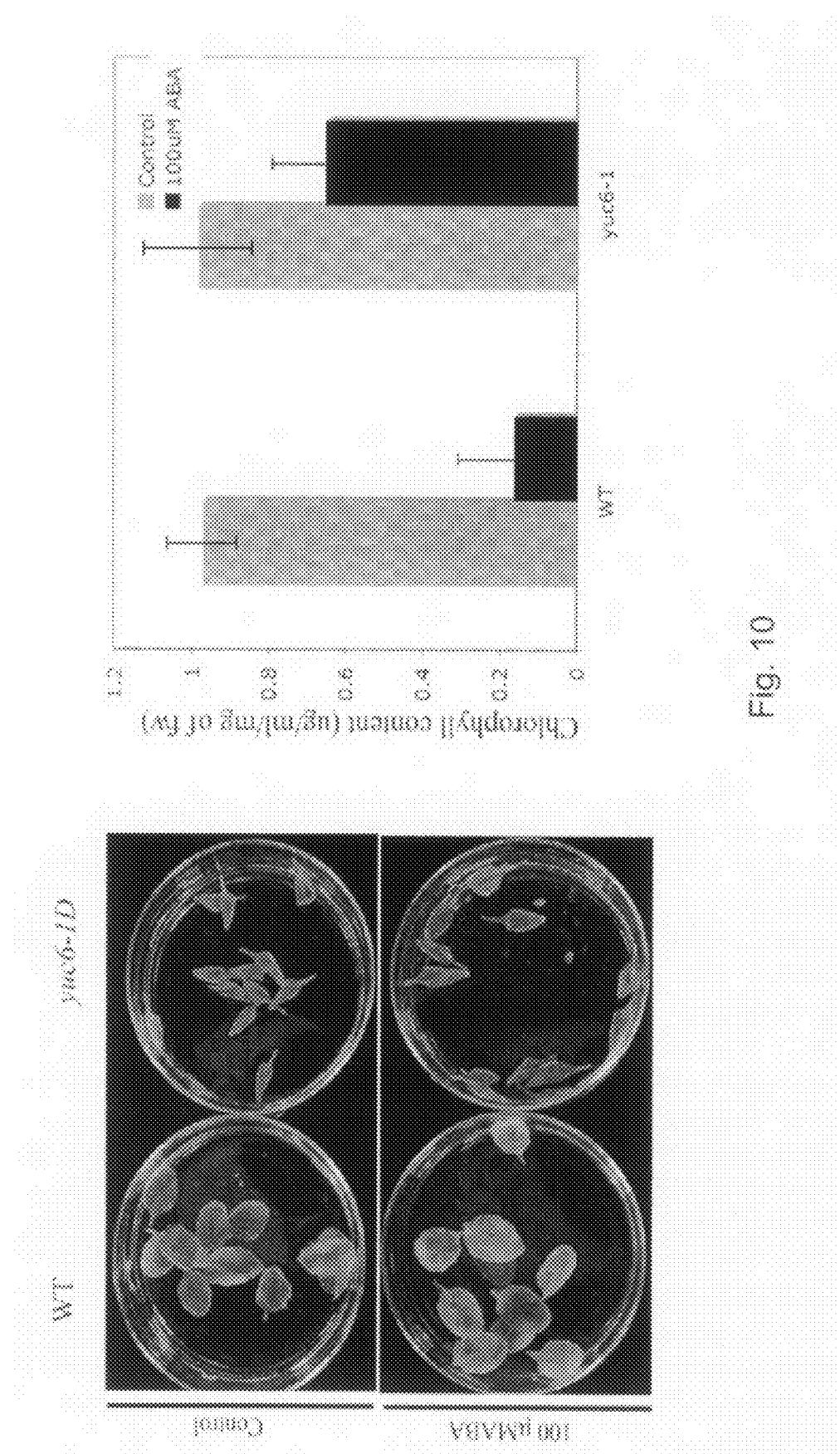

FIG. 10 shows yucca6-1D mutants resistant to ABA induced senescence (comparing wild-type and yucca6-1D mutant). On the left side of FIG. 10, ABA (Abscisic Acid) induced senescence assay with wild-type (left-side) and yucca6-1D (right-side) rosette leaves were performed with $3^{rd}$ to $5^{th}$ rosettes from 3.5-week old soil grown plants. Detached leaves were incubated in 3 mM MES (pH 5.7) solution with and without (control) 100 μM of ABA for a designated time. On the right side of FIG. 10, the cholorphyll content (ug/ml/mg of fresh weight) is shown for both the wild-type and yucca6-1D plants, with and without ABA.

Figure 11:
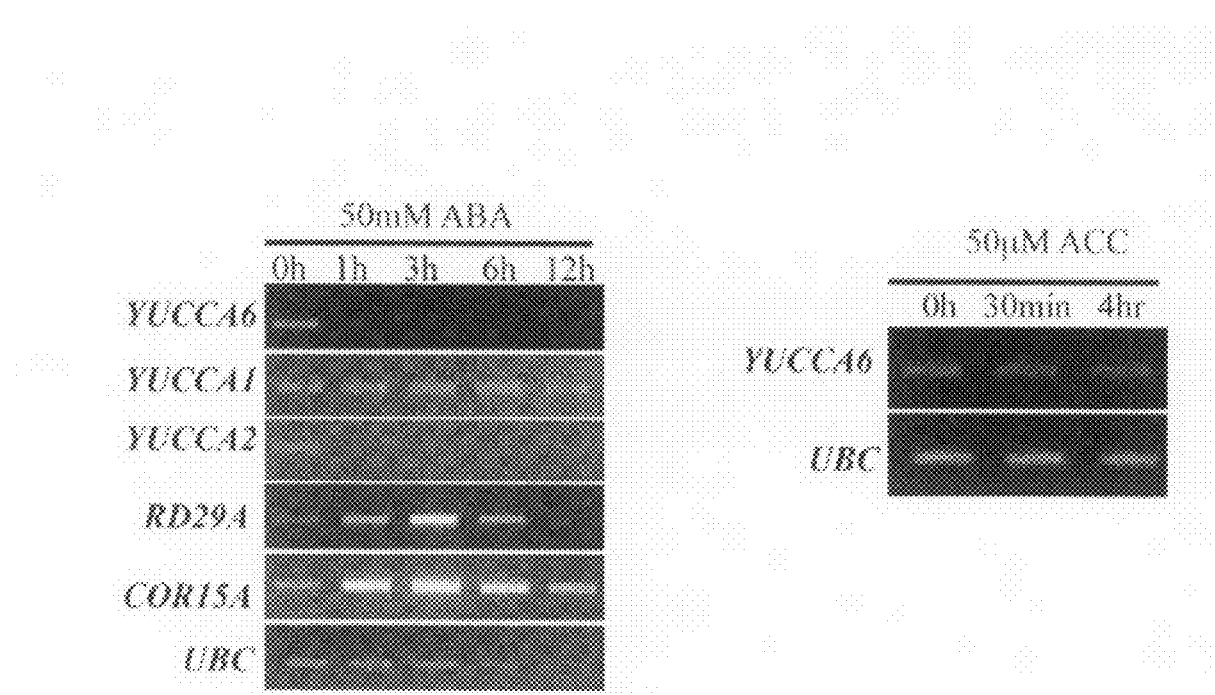

FIG. 11 shows that ABA down-regulates YUCCA6 and YUCCA2 gene expression but does not change YUCCA 1 gene expression. YUCCA gene expression was checked by RT-PCR. RNA was prepared from 2-week old seedlings including roots. RD29A and COR15A were used as positive controls (they are known to be up-regulated during ABA treatment). UBC was used as a loading control.

DETAILED DESCRIPTION OF THE INVENTION

In general the terms and phrases used herein have their art-recognized meaning, which can be found by reference to standard texts, journal references and contexts known to those skilled in the art. The following definitions are provided to clarify their specific use in the context of the invention.

3' non-coding sequence. As used herein, 3' non-coding sequence refers to a DNA sequence located downstream of a coding sequence and preferably includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (Plant Cell (1989) 1:671).

5' untranslated region (5'UTR). As used herein, the 5' untranslated region is the portion of an mRNA from the 5' end to the position of the first codon used in translation.

Altered levels. As used herein, altered levels refer to the production of gene product(s) in transgenic organisms in amounts or proportions that differ from that of normal or non-transformed organisms.

cDNA. As used herein, cDNA refers to a double-stranded DNA that is complementary to and derived from mRNA.

Chimeric gene. As used herein, chimeric gene refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature.

Coding sequence. As used herein, coding sequence refers to a DNA sequence that encodes a specific amino acid sequence.

Constitutive promoter. Promoters which cause a gene to be expressed in most cell types at most times are commonly referred to as constitutive promoters.

Contact(ing). As used herein, the term contact or contacting refers to any means of introducing a vector(s) into a plant cell, including by chemical or physical means.

Delayed senescence. As used herein, delayed senescence is used to describe a plant, whereby leaf senescence is delayed compared to a standard reference.

Drought condition. As used herein, drought condition refers to the growth condition of a plant for a certain period of time without water.

Drought tolerant. As used herein, drought tolerant (or tolerance) refers to plants that can survive under water deficiency conditions.

Endogenous gene. As used herein, endogenous gene refers to a native gene in its natural location in the genome of an organism.

Enhancer. As used herein, an enhancer is a DNA sequence which can stimulate promoter activity and may be an innate element of the promoter or a heterologous element inserted to enhance the level or tissue-specificity of a promoter.

Expression. As used herein, expression refers to the transcription and stable accumulation of sense (mRNA) or anti-sense RNA derived from the nucleic acid fragment of the invention. Expression may also refer to translation of mRNA into a polypeptide.

Expression vector encoding at least one FMO. As used herein, the term "expression vector encoding at least one FMO" refers to an expression vector comprising a nucleotide sequence encoding an FMO polypeptide.

Flavin monooxygenase-like protein (FMO). As used herein, the term flavin monooxygenase-like protein or FMO means an enzyme that is similar to flavin monooxygenase and has oxygenase activity. FMOs described herein include FMOs and homologs thereof isolated from *Arabidopsis thaliana*, rice or other plant species, wherein enhanced expression of these sequences produces the yucca mutant phenotype as described herein.

Foreign gene. As used herein, foreign gene refers to a gene not normally found in the host organism, but that is introduced into the host organism by gene transfer. Foreign genes can comprise native genes inserted into a non-native organism, or chimeric genes.

Gene. As used herein, gene refers to a nucleic acid fragment that expresses a specific protein, preferably including regulatory sequences preceding (5' non-coding sequences) and following (3' non-coding sequences) the coding sequence.

HYT-1 and hyt1-1D and hyt1-2D. As used herein, HYT-1 refers to YUCCA6; hyt1-1D refers to yucca6-1D; hyt1-2D refers to yucca6-2D.

Marker. As used herein, the term marker refers to a gene encoding a trait or a phenotype which permits the selection of, or the screening for, a plant or plant cell containing the marker.

Messenger RNA (mRNA). As used herein, messenger RNA (mRNA) refers to the RNA that is without introns and that can be translated into protein by the cell.

Native gene. As used herein, native gene refers to a gene as found in nature with its own regulatory sequences.

Operably linked. As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

Overexpression. As used herein, overexpression refers to the production of a gene product in transgenic organisms that exceeds levels of production in normal or non-transformed organisms.

Plant. As used herein, the term plant refers to a whole plant, a plant part, a plant cell, or a group of plant cells, such as plant tissue. Plantlets are also included within the meaning of "plant". Plants included in embodiments of the invention are any plants amenable to transformation techniques, including angiosperms, gymnosperms, monocotyledons and dicotyledons.

Promoter. As used herein, promoter refers to a DNA sequence capable of controlling the expression of a coding sequence or functional RNA. In general, a coding sequence is located 3' to a promoter sequence. The promoter sequence preferably consists of proximal and more distal upstream elements, the latter elements often referred to as enhancers. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. New promoters of various types useful in plant cells are constantly being discovered; numerous examples may be found in the compilation by Okamuro and Goldberg (Biochemistry of Plants (1989) 15:1-82). It is further recognized that since in most cases the exact boundaries of regulatory sequences have not been completely defined, DNA fragments of different lengths may have identical promoter activity.

RNA transcript. As used herein, RNA transcript refers to the product resulting from RNA polymerase-catalyzed transcription of a DNA sequence. When the RNA transcript is a perfect complementary copy of the DNA sequence, it is referred to as the primary transcript or it may be an RNA sequence derived from post-transcriptional processing of the primary transcript and is referred to as the mature RNA.

Start codon. As used herein, start codon is a term used to describe a group of three adjacent nucleotides, ATG, (AUG in mRNA) coding for methionine that initiates polypeptide formation.

Stay-green. As used herein, stay-green is a term used to describe a plant phenotype, e.g., whereby leaf senescence (most easily distinguished by yellowing of the leaf associated with chlorophyll degradation) is delayed compared to a standard reference. See, Thomas H and Howarth C J (2000) "Five ways to stay green" Journal of Experimental Botany 51: 329-337.

Stay-green long life. As used herein, stay-green long life is a term used to describe one of the five stay-green categories wherein not all of the stay-green mutants live longer than wild-type plants. See, Thomas H and Howarth C J (2000) "Five ways to stay green" Journal of Experimental Botany 51: 329-337.

Suitable regulatory sequences. As used herein, suitable regulatory sequences refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

Transformation. As used herein, transformation refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al., Meth Enzymol (1987) 143:277) and particle-accelerated or "gene gun" transformation technology (Klein et al., Nature (1987) 327:70-73; U.S. Pat. No. 4,945,050).

Transgene. As used herein, a transgene is a gene that has been introduced into the genome by a transformation procedure.

For purposes of describing embodiments of the present invention, YUCCA6 denotes the FMO gene from *Arabidopsis thaliana* whose enhanced expression leads to the yucca6 mutant phenotype. The product of the YUCCA6 gene (SEQ ID NO:4) is the YUCCA6 protein with the amino acid sequence of SEQ ID NO:1, which has homology to flavin-containing monooxygenases (FMOs) and exhibits FMO enzymatic activity against suitable substrates.

Enhanced expression in plants of FMOs is believed to produce the yucca mutant phenotype as described below. FMOs described herein include FMOs and homologs thereof isolated from *Arabidopsis thaliana*, rice or other plant species, wherein enhanced expression of these sequences produces the yucca mutant phenotype as described below. Identification of additional FMOs that produce the yucca phenotype can be made through cloning techniques known to one of skill in the art, as described more fully in Sambrook et al. (Molecular Cloning: A Laboratory Manual (1989) Cold Spring Harbor Laboratory Press) and Ausubel et al. (Current Protocols in Molecular Biology (1994-1998) John Wiley and Sons (with updates)).

Embodiments of the invention that include host cells or host organisms of the invention include, but are not limited to, plant cells as well as microorganisms such as yeast and bacteria. The expression vector of the invention includes, but is not limited to, plasmid and phage expression vectors suitable for expression in plants, yeast, or bacteria. Embodiments of the present invention provide methods of exposing a substrate molecule to FMOs, where the FMOs may be found in an extract of transformed plant material expressing the FMOs, or the FMOs may be further purified. An extract containing FMOs may be a cell-free extract, or may be substantially cell-free.

Standard recombinant DNA and molecular cloning techniques used herein are well known in the art and are described more fully in Sambrook et al. (Molecular Cloning: A Laboratory Manual (1989) Cold Spring Harbor Laboratory Press: Cold Spring Harbor).

Plants included in embodiments of the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beats, eggplant, spinach, cucumber, squash, melons, cantaloupe, sunflowers and various ornamentals. Woody species include poplar, pine, *sequoia*, cedar, oak, etc.

Genetically modified plants are produced by contacting a plant cell with a nucleic acid construct as described above. In one embodiment the construct is contained within a vector. Vector(s) employed for transformation of a plant cell for shoot meristem expression comprise a nucleic acid sequence comprising at least one structural gene expressing a product of interest, operably associated with the promoter of the invention. The vector harbouring the heterologous nucleic acid sequence can also contain one or more selectable marker genes so that the transformed cells can be selected from non-transformed cells in culture, as described herein.

As used herein, the term "marker" refers to a gene encoding a trait or a phenotype which permits the selection of, or the screening for, a plant or plant cell containing the marker. In one embodiment the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-beta-phosphotransferase, thymidine kinase, exanthineguanine phospho-ribosyltransferase and amino-glycoside 3'-O-phosphotransferase II. Other suitable markers will be known to those of skill in the art.

To commence a transformation process it is conventional to construct a suitable vector and properly introduce it into the plant cell. The details of the construction of the vectors then utilized herein are known to those skilled in the art of plant genetic engineering.

For example, the nucleic acid sequences can be introduced into plant cells using Ti plasmids, root-inducing (Ri) plasmids, and plant virus vectors. (For reviews of such techniques see, for example, Weissbach & Weissbach, 1988, Methods for Plant Molecular Biology, Academic Press, NY, Section VIII, pp. 421-463; and Grierson & Corey, 1988, Plant Molecular Biology, 2d Ed., Blackie, London, Ch. 7-9, and Horsch, et al., Science, 227:1229, 1985, both incorporated herein by reference).

One of skill in the art will be able to select an appropriate vector for introducing FMO nucleic acid sequences in a relatively intact state. Thus, any vector which results in a plant carrying the introduced nucleic acid construct should be sufficient. Even a naked piece of nucleic acid would be expected to be able to confer the properties of this invention, though at low efficiency. The selection of the vector, or whether to use a vector, is typically guided by the method of transformation selected.

The transformation of plants may be carried out in essentially any of the various ways known to those skilled in the art of plant molecular biology. (See, for example, Methods of Enzymology, Vol. 153, 1987, Wu and Grossman, Eds., Academic Press, incorporated herein by reference).

For example, a construct can be introduced into a plant cell utilizing *Agrobacterium tumefaciens* containing the Ti plasmid. In using an *A. tumefaciens* culture as a transformation vehicle, it is advantageous to use a non-oncogenic strain of *Agrobacterium* as the vector carrier so that normal non-oncogenic differentiation of the transformed tissues is possible. It is also preferred that the *Agrobacterium* harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells (De Framond, Biotechnology, 1:262, 1983; Hoekema, et al., Nature, 303:179, 1983). Such a binary system is preferred because it does not require integration into Ti plasmid in *Agrobacterium*.

Cauliflower mosaic virus (CaMV) may also be used as a vector for introducing a nucleic acid construct of the invention into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

Typically, the nucleic acid construct is introduced into a plant cell by contacting the cell with a vector containing the promoter-nucleic acid sequence encoding the protein of interest construct. As used herein, the term "contacting" refers to any means of introducing the vector(s) into the plant cell, including chemical and physical means as described above. In one embodiment, contacting refers to introducing the nucleic acid or vector into plant cells (including an explant, a meristem, a protoplast or a seed), via *Agrobacterium tumefaciens* transformed with the heterologous nucleic acid as described above.

Auxin plays critical roles in many aspects of plant growth and development. Although a number of auxin biosynthetic pathways have been proposed, their overlapping nature has prevented the clear elucidation of auxin biosynthesis. Recently, *Arabidopsis* mutants with supernormal auxin phenotypes have been reported. These mutants exhibit hyperactivation of genes belonging the YUCCA family, encoding putative flavin monooxygenase enzymes resulting in increased endogenous auxin levels (Zhao et al., 2001; Marsch-Martinez et al., 2002; Woodward et al., 2005). The present invention includes the dominant mutants hypertall1-1D (hyt1-1D or yucca6-1D) and hypertall1-2D (hyt1-2D or yucca6-2D) as new alleles of a member of the *Arabidopsis* YUCCA family. Overexpression of the YUCCA6 gene leads to elevated auxin levels and hyperinduction of several IAA-responsive genes. Although yucca6-1D displays some of the signature phenotypes common to other *Arabidopsis* yucca mutants, unexpectedly the mutant of the present invention also exhibits unique characteristics such as a normal root phenotype, an exceptionally large increase in inflorescence height, altered leaf morphology, an increased tolerance to drought and a delay in senescence (to date no reports of delayed senescence for other members of the YUCCA family are known), which can convey certain desirable agronomic traits. In addition, *Arabidopsis* YUCCA overexpression mutants that have been reported to date exhibit similar but not identical phenotypes (Cheng et al., 2006).

Typically when auxin is overproduced in plants it triggers effects such as aborted inflorescences and adventitious and lateral root formation, which are undesirable from an agronomic perspective (Klee et al., Genes Devel 1: 86-96, 1987; Kares et al., Plant Mol Biol 15: 225-236, 1990). yucca6-1D plants of the present invention display epinastic cotyledons, elongated hypocotyls, and strong apical dominance that are all phenotypes similar to those of other yucca activation mutants (yucca1-5). However, yucca6-1D plants of the present invention unexpectedly do not have short and hairy roots and are not hookless when grown in the dark, which are phenotypes that have been observed in plants containing yucca1. Compared to wild type plants, the yucca6-1D plants of the present invention also display some very unique unexpected mutant phenotypes such as twisted cauline leaves, larger seeds, much more extreme apical dominance, drought tolerance and delayed senescence. The present invention also includes yucca6-2D and 35S:YUCCA6 transgenic plants that have phenotypes consistent with that of yucca6-1D.

Recombinant YUCCA6 protein appears to localize in a cytoplasmic compartment and can catalyze oxygenation of tryptamine, and, thus, YUCCA6 appears to function in Trp-dependent auxin biosynthesis. Unexpectedly, yucca6-1D plants of the present invention are able to survive for up to 5 months longer than wild type plants.

Microarray analyses revealed that expression of several indole-3-acetic acid (IAA) inducible genes, including AUX/IAA, SMALL AUXIN-UP RNA (SAUR), and GH3 is several-fold higher in yucca6 mutants of the present invention than in wild type plants. Tissue explants of yucca6 mutant seedlings can also develop roots or shoots in an auxin-independent manner. Endogenous free IAA levels in yucca6 mutants are also elevated. Results from tryptophan analogue feeding experiments and catalytic activity assays with recombinant YUCCA6 indicate that YUCCA6 is involved in a tryptophan-dependent auxin biosynthesis pathway.

Embodiments of the invention include a plant produced by the method of the invention, including plant tissue, seeds, and other plant cells or parts derived from the plant containing yucca6-1D and/or yucca6-2D and/or 35S:YUCCA6.

EXAMPLES

The following examples are provided for illustrative purposes, and are not intended to limit the scope of the invention as claimed herein. Any variations in the exemplified articles which occur to the skilled artisan are intended to fall within the scope of the present invention.

Example 1

Isolation of the hyt1-1D (yucca6-1D) Mutant

Figure 1:
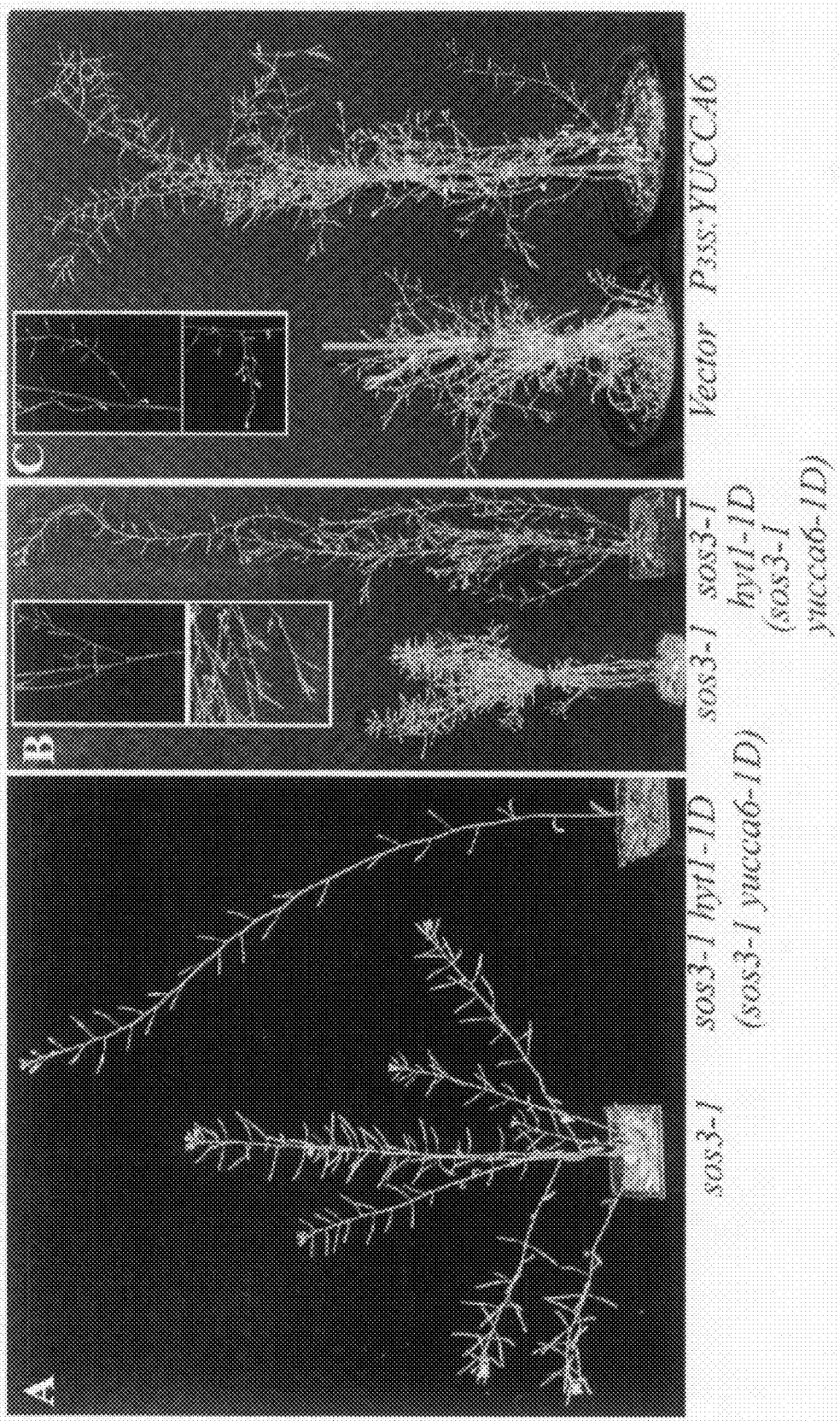
FIGS. 1A-1C shows the morphological phenotypes of sos3-1 yucca6-1D.

The hyt1-1D (yucca6-1D) mutant of the present invention was identified in a root-bending, second-site suppression mutation screen of a T-DNA insertion population (pSKI015) in the *Arabidopsis* Columbia (Col-0) gl1 sos3-1 background (Rus et al., 2001; Miura et al., 2005). During production of T3 lines, it was evident that sos3-1 hyt1-1D plants displayed dramatic developmental alterations compared to the wild type. Eight weeks after germination, plants of sos3-1 hyt1-1D unexpectedly had only one inflorescence, whereas wild-type plants of the same age had at least five (FIG. 1A). Although sos3-1 hyt1-1D mutants eventually formed floral branches, the height of fully grown sos3-1 hyt1-1D plants was unexpectedly over twice that of wild-type plants. From an $F_2$ population of the backcross of sos3-1 hyt1-1D to Col-0 gl1, a single mutant, hyt1-1D, was isolated. The hyt1-1D (yucca6-1D) mutant displayed the same morphological and developmental phenotypes as sos3-1 hyt1-1D (FIGS. 1A and 1B). The $F_2$ generation progeny of the hyt1-1D×Col-0 gl1 line showed a segregation of the hyt1-1D:wild-type phenotypes of 3:1 ($X^2$=0.043; P>0.05), indicating that the hyt1-1D (yucca6-1D) mutation was dominant. In addition, 20-week-old wild-type and sos3-1 yucca6-1D plants as well as 20-week-old transgenic plants with only a vector (Pro35S) or with Pro35S: YUCCA6 produced similar results as the 8-week old plants. sos3-1 hyt1-1D plants remained green and survived at least three to five months longer than wild type (FIG. 1B). To confirm whether overexpression of YUCCA6 caused the yucca6 mutant phenotypes, the coding sequence (SEQ ID NO:2) of YUCCA6 was introduced under the control of the constitutive CaMV35S promoter into wild-type plants, causing overexpression of YUCCA6 transcript. As shown in FIG. 1C, transgenic lines overexpressing YUCCA6 (35S: YUCCA6) also displayed a staygreen-long life phenotype. These results confirmed that staygreen phenotypes observed in the yucca6-1D result from the enhanced accumulation of the YUCCA6 transcript.

Example 2

Plant Material and Growth Conditions

*Arabidopsis thaliana* ecotype Col-0gl1 and Col-0 were used as the wild type of hyt1-1D and hyt1-2D respectively. Plants were grown at 20-23° C. on MetroMix 360 (Scotts) under 16-hour/8-hour light-dark cycle in the greenhouse or growth chamber. For growth analysis, seedlings were grown under sterile conditions on Murashige and Skoog (MS) media plates containing 8% agar and 30 g/l sucrose. For observation of root phenotypes and etiolated hypocotyls, 1.2% agar plates were cultured vertically. Seeds were surface sterilized with 20% bleach for 5 minutes and subsequently washed five times with sterile distilled water. Seeds were cold-treated for 4 days at 4° C. and then plates were placed in a growth room at 22° C. on a 16-hour/8-hour light-dark cycle. For genetic analysis, the genotype of $F_1$ and $F_2$ generation was determined by epinastic cotyledon and long-narrow rosette leaf morphology. For hydroponic culture, 2.5-week old plants were removed from soil and roots were carefully washed with water before transfer to modified Hoagland solution (without aeration) containing 1 mM $KH_2PO_4$ for hydroponic culture (Liu et al 1998). Plants were transferred to a fresh solution twice a week.

The production of an *Arabidopsis thaliana* T-DNA insertion mutant (pSKI015) population of Col-0 gl sos3-1 background and identification of mutations that suppress $Na^+$ hypersensitivity of sos3-1 were as described in (Rus et al 2001).

Example 3

Identification of the T-DNA Insertion Position in the hyt1-1D (yucca6-1D) Mutant The genomic DNA adjacent to the left border of the T-DNA insertion was cloned by thermal asymmetric interlaced PCR.

Figure 2:
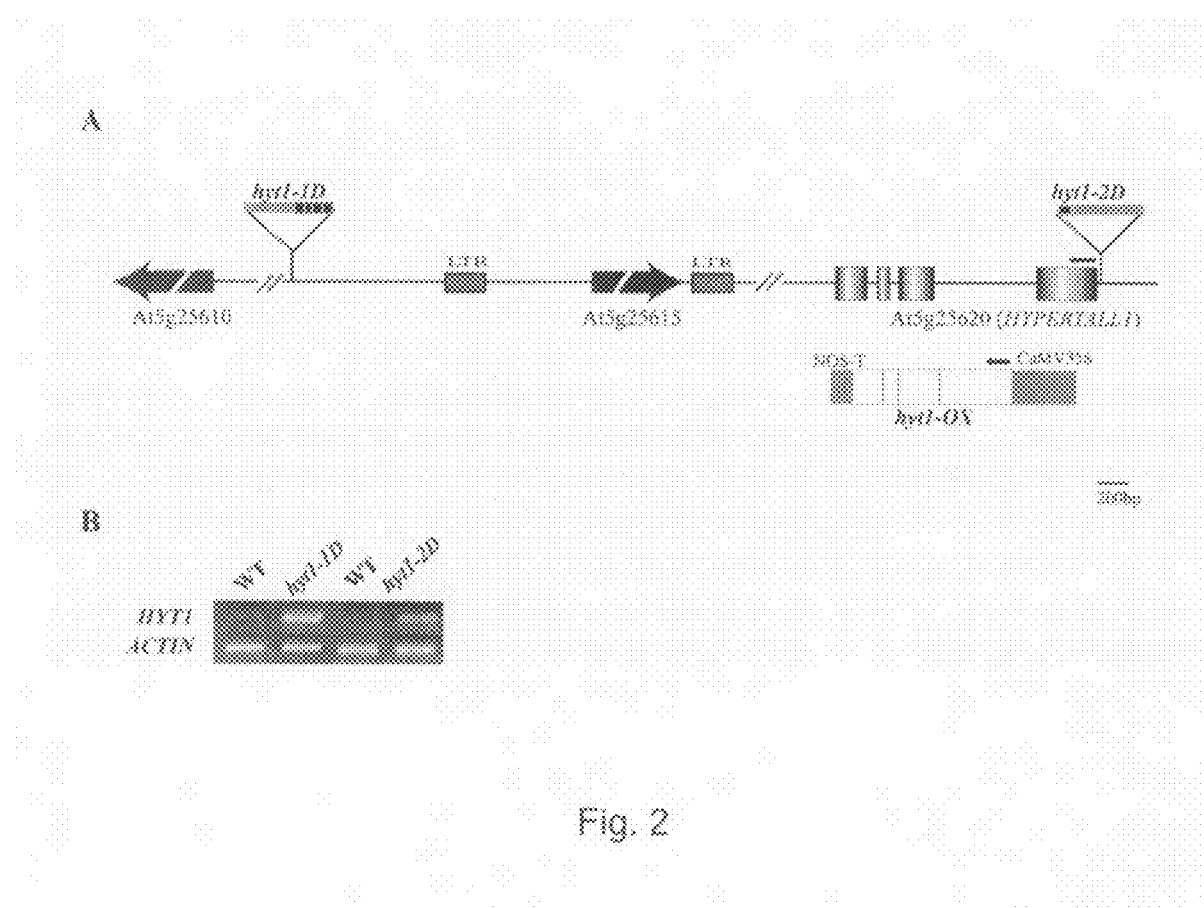
FIGS. 2A-2B shows the schematic diagrams of the genomic organization at the T-DNA insertion sites and transcript level changes.

Perfectly matched sequences were found in the bacterial artificial chromosome clone T14C9. The left border of the T-DNA was inserted at 84,710 nucleotides from the 5' end of T14C9. The open reading frame (ORF) near the left border of the T-DNA encodes a product (At5g25610) with high similarity to RD22 (FIG. 2A). The distance between the T-DNA insertion and the translation start site of this ORF is about 10 kb. No transcriptional change in At5g25610 between the wild type and the hyt1-1D mutant was detected by reverse transcription (RT)-PCR, suggesting that At5g25610 is not involved in the hyt1-1D phenotype. The ORF of the right border of the T-DNA insertion encodes a copia-like retrotransposon (At5g25615; FIG. 2A). The distance between the cauliflower mosaic virus (CaMV) 35S enhancers and the predicted translation start site is about 1.2 kb. Both the 5' and 3' ends of At5g25615 have 337 bp of long terminal repeat (LTR) sequences. Transcripts of At5g25615 as well as the LTR regions accumulated slightly more in hyt1-1D compared to the wild-type. However, introducing into the wild-type plants either cDNA of At5g25615, the LTR region, or the genomic region including the LTR under the control of the CaMV 35S promoter could not recapitulate any phenotype of hyt1-1D, indicating that altered expression of either At5g25615 or the LTR regions does not cause hyt1-1D (yucca6-1D) phenotypes.

Example 4

Identification of the HYT1 Locus

From the result of microarray analyses, we found that the accumulation of transcript of an FMO (At5g25620; GenBank accession no. NC_003076 incorporated herein) in the mutant plant of the present invention was 9.8-fold higher than in the wild-type plant. The distance between the CaMV 35S enhancers and the predicted translation start site of At5g25620 was about 11 kb. RT-PCR confirmed that the transcript of this FMO-like gene accumulated to high levels in hyt1-1D (FIG. 2B), indicating that overexpression of the FMO-like protein could be the locus responsible for the hyt1-1D phenotypes.

Figure 3:
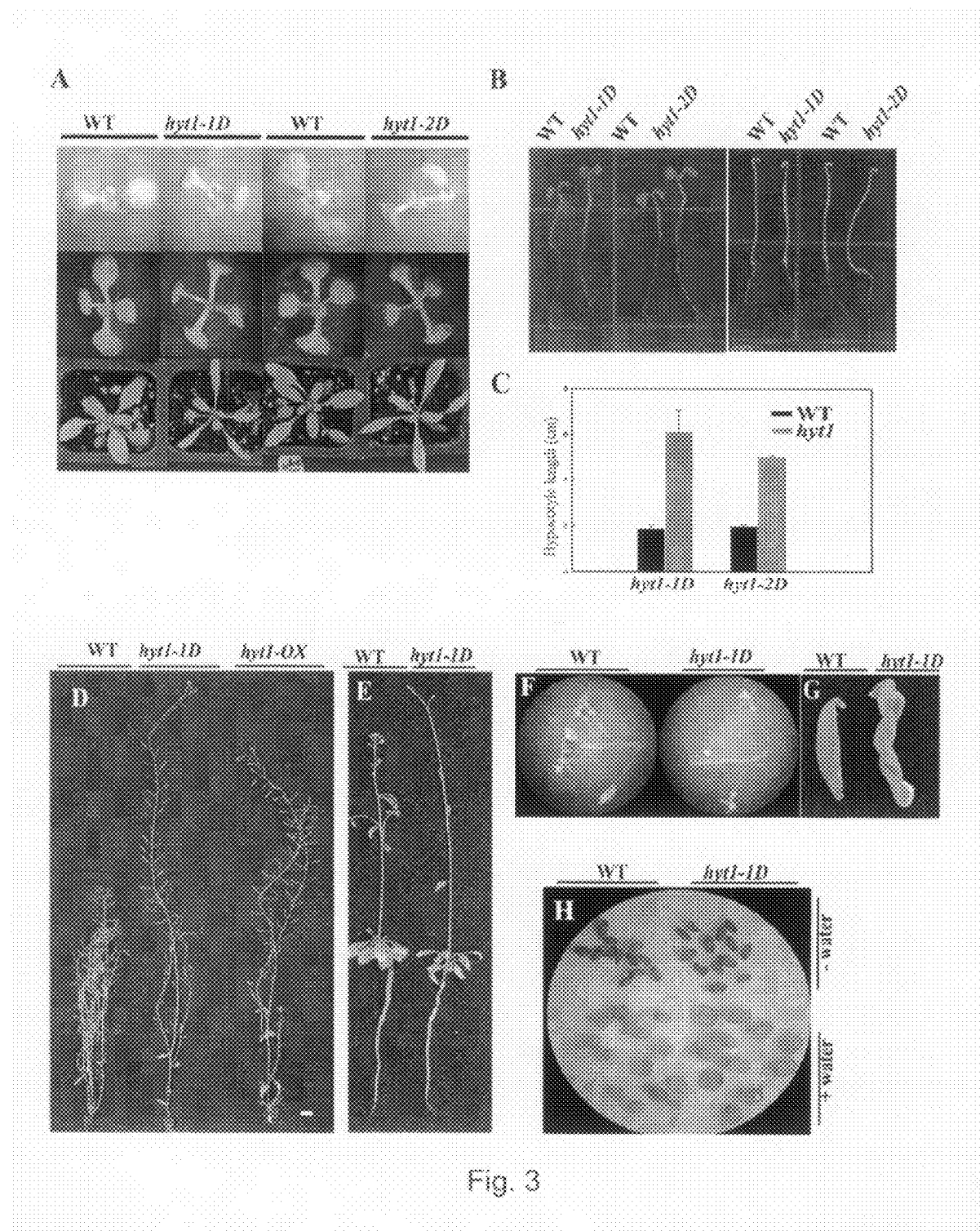
FIGS. 3A-3H shows the analysis of the hyt1-1D (yucca6-1D) and hyt1-2D (yucca6-2D) mutant phenotypes.

From the Salk Institute Genome Analysis Laboratory database (Alonso et al., 2003), we identified SALK_019589 that was revealed by diagnostic PCR to have a T-DNA insertion that included an intact 35S promoter in the 5'-untranslated region of At5g25620. Transcript of the FMO in SALK_019589 also accumulated to a high level compared to that in wild-type plants (FIG. 2B). SALK_019589 also displayed similar morphological phenotypes as hyt1-1D (yucca6-1D) (FIG. 3A). At5g25620 was annotated as HYT1, and SALK_019589 was designated as hyt1-2D (yucca6-2D) as an allele of HYT1.

Example 5

Isolation of hyt1-1D (yucca6-1D) and hyt1-2D (yucca6-2D) Single Mutants

DNA flanking the left border of the inserted T-DNA in sos3-1 hyt1-1D plants was isolated by thermal asymmetric interlaced PCR (Liu et al., 1995) and the entire isolated fragment was sequenced. The following primer pairs were designed to determine the homozygous hyt1-1D mutant of the present invention: forward, 5'-TGGTACTAATTCAGCAAT-3' (SEQ ID NO:5); reverse, 5'-ACTCTACGTACATTGAAG-3' (SEQ ID NO:6). To isolate a single hyt1-1D mutant from sos3-1 hyt1-1D, sos3-1 hyt1-1D was crossed into Col-0 gl1 and a single mutant from the $F_2$ generation pool was selected having the hyt1-1D phenotype without the sos3 mutation through diagnostic PCR using the following primer sets: for primer set 1 which is complementarily bound to the wild-type non-deleted sequence, forward, 5'-ATGTGCTTTCAAGTTGTACG-3' (sos-primer1) (SEQ ID NO:7), reverse, 5'-TTTATCTTTCCTTGCATGGC-3' (sos-primer2) (SEQ ID NO:8); and for primer set 2, which allows recognition of the deleted sequence of SOS3, forward, 5'-GCATGTGCTTTCAAGTTACG-3' (sos-primerfor) (SEQ ID NO:9), reverse, 5'-TTTATCTTTCCTTGCATGGC-3' (sos-primerrev) (SEQ ID NO:10). hyt1-2D allele in the Col-0 background was identified in the Salk Institute Genome Analysis Laboratory database, and $T_3$ seeds were provided by the Salk Institute laboratory through the *Arabidopsis* Biological Resource Center at The Ohio State University. A homozygous line of hyt1-2D was selected by performing PCR using the following primer set: 5'-GTATGCAGCCATTGGTTGATC-3' (LP) (SEQ ID NO:11); 5'-CGGTCATAAGTCTTGAGCTGC-3' (RP) (SEQ ID NO:12) and 5'-TGGTTCACGTAGTGGGCCATCG-3' (LBa1) (SEQ ID NO:13).

Example 6

RNA Preparation and Expression Analysis

Total RNA was extracted from designated tissues using RNeasy Plant Mini Kit (QIAGEN). After treatment with DNaseI (INVITROGEN), 2 µg of total RNA was used for the synthesis of the first-strand cDNA using THERMOSCRIPT RT-PCR system and oligo dT as primers (INVITROGEN). The gene specific primers used to detect the transcripts were as follows: YUCCA6 forward primer, 5'-ATGGATTTCTGTTGGAAGAGAGAG-3' (SEQ ID NO:14), YUCCA6 reverse primer, 5'-TCAGATTTTTTTTACTTGCTCGTCT-3' (SEQ ID NO:15); UBC (At5g25760) forward primer 5'-ATACAAAGAGGTACAGCGAG-3' (SEQ ID NO:16), reverse primer 5'-TTCTTAGGCATAGCGGCG-3' (SEQ ID NO:17); GH3 (At5g54510) forward primer 5'-CGGACAAAACCGATGAGGTTG-3' (SEQ ID NO:18), reverse primer 5'-ACTCCCCCATTGCTTGTGACC-3' (SEQ ID NO:19); GH3 (At2g23170) forward primer 5'-GCATTGAGTCGGATAAAACCGATG-3' (SEQ ID NO:20), reverse primer 5'-TCAACGACGACGTTCTGGTGAC-3' (SEQ ID NO:21); and IAA1 (At4g14560) forward primer 5'-ATGGAAGTCACCAATGGGCTTAAC-3' (SEQ ID NO:22), reverse primer 5'-CATAAGGCAGTAGGAGCTTCGGATC-3' (SEQ ID NO:23).

Example 7

HYT1 is a Member of the YUCCA Gene Family

Sequence analysis of the HYT1 cDNA clone showed that it encodes a 418-amino acid putative flavin-containing monooxygenase. Phylogenic tree analysis indicated that HYT1 is one of 11 *Arabidopsis* YUCCA-like family genes and belongs to the YUCCA2 sub-family (Cheng et al., 2006). In comparison with other YUCCA family genes, HYT1 has 48.5% amino acid identity with YUCCA1 and 61.0% amino acid identity with YUCCA2. The ORFs of HYT1, YUCCA 1, and YUCCA2 from *Arabidopsis* and FLOOZY (FLZ) from petunia are interrupted by three introns. Similar to YUCCA1, YUCCA5, and FLZ, the HYT1 protein contains conserved binding motifs (GAGPSG) for FAD and (GCGNSG) for NADPH. HYT1 and hyt1-1D, hyt1-2D were renamed YUCCA6 and yucca6-1D, yucca6-2D, respectively, following the nomenclature of the YUCCA family genes. Yucca6-1D and yucca6-2D are transgenic plants having enhanced YUCCA6 expression.

Example 8

Overexpression of YUCCA6 Recapitulates the yucca6-1D Phenotype

To confirm whether overexpression of YUCCA6 caused the yucca6 mutant phenotypes, the cDNA of YUCCA6 of the present invention was introduced under the control of the constitutive CaMV 35S promoter into wild-type plants, causing overexpression of YUCCA6 transcript (FIG. 2A). In FIG. 3D for example, transgenic plants exhibited yucca6 mutant phenotypes such as epinastic cotyledons, long hypocotyls, long narrow leaves with elongated petioles, and strong apical dominance. These results confirmed that phenotypes observed in yucca6-1D and yucca6-2D result from the enhanced accumulation of YUCCA6 transcript.

Example 9

Generation of YUCCA6 Overexpression Transgenic Plants

YUCCA6 cDNAs were amplified by PCR with the following primer set: forward primer, 5'-CTCTAGAATG-GATTTCTGTTGGAAGAGA-3' (BamH1H-yucca6-F) (SEQ ID NO:24); reverse primer, 5'-CCTGCAGTCA-GATTTTTTTTACTTGATC-3' (PstI-yucca6-R) (SEQ ID NO:25). PCR products were confirmed by nucleotide sequencing and were cloned into binary vector PCAMBIA1300-PT between the PstI and the BamHI sites, and the identity of the clone insert was confirmed by sequencing. The binary vector pCAMBIA1300-PT is a pCAMBIA1300-based vector containing modified enzyme sites. The construct was introduced into Col-0 μl wild-type plants through an *Agrobacterium tumefaciens*-mediated (strain GV3101) floral dipping transformation method (Clough et al. 1998. Plant J. 16:735-743). Primary transformants were isolated on MS medium containing 30 mg/L hygromycin (INVITROGEN) and transferred to soil to grow to maturity.

Example 10

The Dominant Mutation of YUCCA6 Confers Traits Unique among YUCCA Family Members Homozygous yucca6-1D and yucca6-2D plants of the present invention showed pleiotropic effects at several stages of plant development. Both yucca6-1D and yucca6-2D seedlings exhibited epinastic cotyledons and narrow, long rosette leaves with downward curled edges, and elongated petioles (FIG. 3A). The hypocotyl lengths of yucca6-1D and yucca6-2D were 3.2 (yucca6-1D) and 2.5 times (yucca6-2D) longer than the wild-type seedlings, respectively, under long-day conditions (FIG. 3C). Mature plants produced a strong apically dominant inflorescence (FIG. 3D). Such phenotypes are similar to IAA overproduction mutants, such as yucca1, yucca4, FZYox, sur1, sur2, and CYP79B2oX (Boerjan et al., 1995; King et al., 1995; Barlier et al., 2000; Zhao et al., 2001, 2002; Marsch-Martinez et al., 2002; Tobeña-Santamaria et al., 2002). However, several unique traits were observed in yucca6 mutants. Although short, hookless, etiolated hypocotyls and short, hairy roots are phenotypes commonly found in IAA overproduction mutants (Boerjan et al., 1995; Delarue et al., 1998; Zhao et al., 2001; Smolen and Bender, 2002; Tobeña-Santamaria et al., 2002), unexpectedly these phenotypes were not evident in yucca6-1D and yucca6-2D (FIG. 3B). Root length and lateral root number of yucca6 seedlings were not different from the wild type when grown in solid Murashige and Skoog (MS) media or in hydroponic conditions (FIGS. 3B and 3E). However, yucca6 plants of the present invention were at least twice as tall as wild-type plants (FIG. 3D). The pedicel length and distance between siliques on the main inflorescence of yucca6-1D mutants were longer than the wild type, and yucca6-1D had more bud clusters than the wild type (FIG. 3F). The seed size of yucca6-1D was also slightly larger than the wild type, especially after imbibing water (FIG. 3H). In addition, mature cauline leaves of 8-week-old yucca6-1D were severely twisted (FIG. 3G).

Example 11

Figure 4:
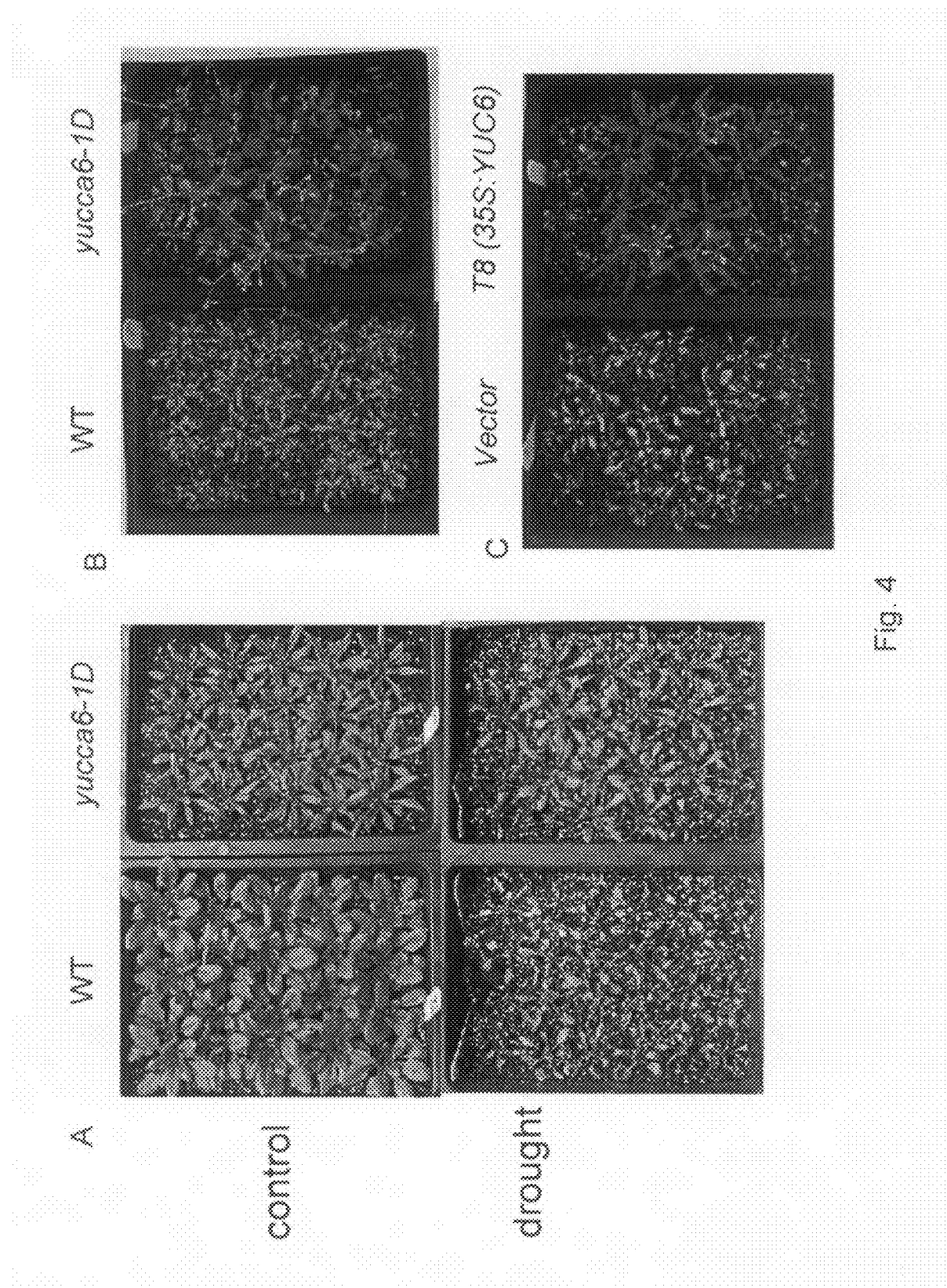
FIGS. 4A-4C shows overexpression of YUCCA6 causes resistance to drought stress.

Knock-out Mutant in YUCCA6 is Sensitive to Drought Stress While Activation Mutant is Tolerant to Drought Stress Stay-green plants usually display drought resistant phenotypes. Overexpression of YUCCA6 causes resistance to drought stress. Wild-type and yucca6-1D 3 week-old soil grown plants were grown under water deficiency (drought conditions) and well-watered conditions (control) for 12 days. The yucca6-1D plants were able to survive the drought conditions while the wild-type plants could not (FIG. 4A).

yucca6-2D, is a second allele of yucca6-1D. yucca6-2D plants also have activation of YUCCA6 though at a level of activation that is lower than yucca6-1D. yucca6-2D also showed a drought resistant phenotype compared to wild-type (FIG. 4B). In addition, a transgenic plant with 35S:YUCCA6 also grown under water deficiency conditions (drought conditions) for 10 days displayed similar drought resistant phenotypes to yucca6-1D (FIG. 4C).

Knock-out of YUCCA6 causes sensitivity to drought stress. Wild-type and yucca6-3k (knock-out mutant also known as a loss-of-function mutant, the YUCCA6 transcript does not appear in this mutant) 3 week-old soil grown plants were grown under water deficiency (drought conditions) and well-watered conditions (control) for 12 days. The knock-out of YUCCA6 caused a sensitive phenotype to drought stress compared to wild-type (FIG. 5).

Wilting phenotypes were observed during water deficiency (drought conditions). yucca6-1D (overexpression mutant) and yucca6-3k (knock-out) mutant were grown under water deficiency (drought conditions) and well-watered (control) conditions for 12 days along with wild-type. Drought resistant phenotypes were observed in the yucca6-1D plants during drought conditions, while drought sensitive phenotypes were observed in yucca6-3k plants during drought conditions. In addition, when wild-type plants display wilting during drought, the yucca6-1D plants did not. Also, yucca6-3k plants wilted faster than wild-type plants (FIG. 6). These results indicate that YUCCA6 is involved in the drought response process.

Example 12

Delayed Senescence Phenotype of yucca6 Mutant

Figure 7:
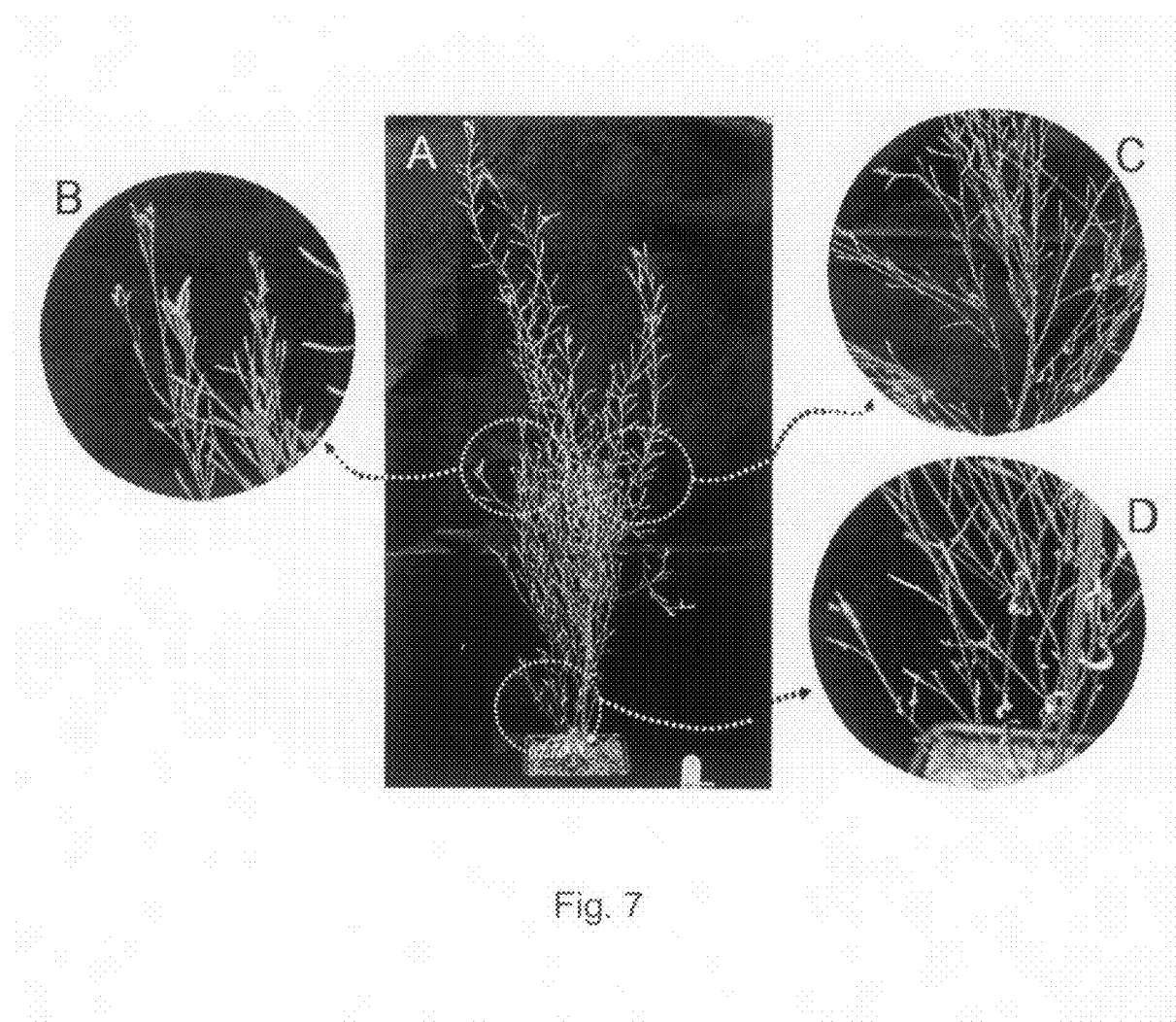

As seen in FIG. 7, a 20-week-old soil-grown yucca6-1D plant of the present invention unexpectedly stayed green and made new shoots and flowers while wild-type plants died (wild-type plants not shown in FIG. 7). In addition, the delayed senescence phenotype was also detected in a transgenic plant having 35S:YUCCA6 (after 20 weeks of growth), whereas a transgenic plant transformed with the vector alone did not have the delayed senescence phenotype (FIG. 8; vector only on the left panel and 35S:YUCCA6 on the right panel).

SAG12 (Senescence Associated Gene 12) transcripts are known to be up-regulated during senescence. Expression level of the SAG12 transcript in wild-type and a yucca6-1D mutant was detected by RT-PCR using RNA extracted from a 35-day old and 50-day old soil grown wild-type and yucca6-1D plants. The result showed that expression levels of the SAG12 transcript from the yucca6-1D mutant plants (35-day old and 50-day old) are lower than from the wild-type plants (FIG. 9). The results indicate that activation of YUCCA6 causes delayed senescence at the molecular level.

yucca6-1D mutants also show resistance to hormone- and dark-induced senescence. Age as well as some hormones is known to be involved in senescence, especially the well-known senescence acceleration hormones Ethylene, Jasmonic Acid and Abscisic Acid (ABA). Hormone- and dark-induced senescence assays with wild-type and yucca6-1D mutant rosette leaves were performed with the $3^{rd}$ and $5^{th}$ rosettes from 3.5-week old soil-grown plants. The detached leaves were incubated in 3 mM MES (pH 5.7) solution with and without 50 µM of ACC (1-aminocylopropane-1-carboxylic acid) and 50 µM of Methyl Jasmonic acid for 3, 4 or 6 days (16 hours light and 8 hours dark). More yellowing of leaves occurred in the wild-type plants compared to the yucca6-1D plants. When the detached leaves were kept under dark conditions, yucca6-1D leaves displayed delayed senescence. These results imply that activation of YUCCA6 is involved in hormone-induced senescence, dark-induced senescence as well as age-dependent senescence.

yucca6-1D mutants also show resistance to ABA-induced senescence. An ABA-induced senescence assay with wild-type and yucca6-1D rosette leaves were performed with the $3^{rd}$ to $5^{th}$ rosettes from 3.5-week old soil-grown plants. The detached leaves were incubated in 3 mM MES (pH 5.7) solution with and without 100 µM of Methyl Jasmonic acid for designated time. When ABA was added yucca6-1D mutants showed resistance to ABA-induced senescence than wild-type (FIG. 10).

*Arabidopsis* YUCCA6 is one of 11 yucca family members. YUCCA6 belongs to the same sub-family with YUCCA2. We determined if YUCCA6 gene expression is regulated by ABA. We found only YUCCA6 and YUCCA2 that are in the same sub-family were down-regulated by ABA treatment (FIG. 11). RD29A and COR15A were used as positive controls (they are known to be up-regulated during ABA treatment). However, ACC (which gets converted to Ethylene) could not regulate YUCCA6 transcript levels. These results imply that YUCCA6 is involved in senescence through ABA but not through Ethylene. It is known that auxin induces ethylene production, but epinastic leaves, elongated hypocotyls, and increased apical dominance were shown to be independent of putative secondary ethylene effects resulting from auxin induced ethylene production (Romano et al., 1993).

Example 13

Overexpression of YUCCA6 Induces IAA-REGULATED Genes and Elevates Auxin Levels

From microarray analyses, expression of several IAA-inducible genes, including Aux/IAA, SAUR, and GH3, was found to be several fold higher in yucca6 mutants than that in the wild-type. The elevated transcript levels of GH3 and IAA1 were confirmed by RT-PCR analysis. Using the DR5: GUS maximal auxin reporter (Ulmasov et al., 1997), IAA levels were estimated by GUS staining in planta. Strong GUS expression in the cotyledon, rosettes, and hypocotyls in DR5: GUS/yucca6-1D was observed, indicating increased endogenous IAA levels. In addition, the ability of elevated auxin levels in yucca6-1D to function physiologically in vivo was tested with an auxin dependency assay in callus culture. When yucca6-1D explants were grown in MS medium, root growth was observed in yucca6-1D explants but not in wild-type explants. Also, yucca6-1D explants cultured in MS media containing cytokinin could produce callus and regenerate shoots, whereas wild-type explants could not. Endogenous free IAA levels were also measured in the yucca6 mutant and in wild-type plants at different developmental stages and tissues. Five-day-old yucca6 mutant seedlings contained similar amounts of free IAA compared to wild-type seedlings. Six-week-old upper inflorescences and cauline leaves of yucca6 mutants also contained higher levels of auxin than wild-type plants. However, free auxin levels in 10-day-old yucca6 seedling roots were not different from the wild type. Free auxin was increased 25% in shoots. Inflorescences (including flowers) of yucca6 mutants contained 32% more free IAA than the wild type, and the free IAA levels were increased 91% in cauline leaves, which had a dramatically altered morphological phenotype compared to the wild type. Thus, the organs exhibiting strong phenotypic alterations, such as cauline leaves and inflorescences, also exhibited the greatest increases in auxin levels, whereas the root system that did not exhibit any phenotype changes showed no significant changes in auxin levels (FIGS. 3B and 3E).

Histochemical GUS Analysis: Ten-day-old seedlings grown on MS media were incubated overnight in 1 mM X-gluc (5-bromo-4-chloro-3-indolyl-C-D-glucuronide; Rose Scientific) and 0.1 M potassium phosphate buffer, pH 7.5, with 0.1% Triton X-100 (Jefferson et al., 1987). Chlorophyll was removed by washing plants several times with 70% ethanol.

Example 14

Microarray Evaluation and Statistical Analysis

Total RNA was isolated by a method developed for tissues with high carbohydrate content (Jaakola et al., 2001. Mol. Biotechnol. 19:201-204). RNAs (70 µg each) from ambient and elevated $CO_2$ treatments were reverse transcribed (SuperScript III; Invitrogen) and cDNAs labelled with Cy3 or Cy5 by indirect labelling (Miyazaki et al., 2004. Field Crops Res 90:47-59). Microarray slides with >26,000 DNA elements (70-mer gene-specific oligonucleotides; Qiagen/Operon) were used (Miyazaki et al., 2004). To avoid bias in microarrays as a consequence of dye-related differences in labelling efficiency, dye labelling for each paired sample (mutant/control) was swapped. Two biological repeats were carried out.

Signal intensities for each array element were collected (GenePix 4000B, Axon Instruments) and images analyzed (GENEPIX Pro 4.0). Spots with intensities lower than background or with an aberrant spot shape were flagged by the GENEPIX software and checked manually. The resulting GPR files were converted by EXPRESSCONVERTER V.1.5 and analyzed by the TIGR-TM4 package (Saeed et al., 2003. Biotechniques 34:374-378). Total intensity normalization, Lowess (Locfit) normalization, SD regulation, and intensity filtering were done within each slide by TM4-MIDAS (version 2.18). Statistical analyses were carried out using TM4-MEV (ver. 3.0.3). In MEV, a one-class t test with P=0.01 was carried out to reveal patterns of regulation (Hegde et al., 2000. Biotechniques 29:548-550; Gong et al., 2005. Plant J 44:826-839).

Example 15

Quantification of Free IAA Levels

Free IAA determinations of seedlings were performed as described in Geisler et al. (2005). Assays of mature aerial plant tissues were performed in a similar manner but utilized 25 mg of excised tissue (from five plants) for each sample. Three sets of sampled sections were assayed for each auxin determination. Briefly, the tissue was homogenized in liquid nitrogen, diluted with 800 μL 0.05 M sodium phosphate, pH 7.0, 0.02% (w/v) sodium diethyldithiocarbamate, combined with 4 ng $^{13}$C[IAA] working standard, shaken for 15 min at 4° C., and combined with 40 μL of 1 M HCl (depending on starting weight of plant material) to a final pH of 2.7. Samples were then passed through a 0.45-μm syringe filter and applied to an Isolute C8EC (500 mg/3 mL; no. 291-0050-B) solid-phase extraction column preconditioned by methanol/acetic acid. The sample was washed with 2 mL 10% MeOH/1% AcOH, vacuumed to remove water phase (without drying), and eluted into derivatization vials with 1 mL 70% methanol/1% acetic acid. The samples were vacuum evaporated to dryness at 30° C. and methylated by adding 200 μL methanol, 1 mL dichloromethane, and 5 μL 2 M trimethylsilyldiazomethane (in hexanes), followed by incubation at 42° C. for 30 min. After neutralization with 5 μL of 2 M acetic acid/hexane to destroy excess diazo-methane, samples were evaporated to dryness and resuspended in acetonitrile. Samples were analyzed by gas chromatography-mass spectrometry as described by Ljung et al. (2005. Plant Cell 17:1090-1104), except that an Agilent/LECO gas chromatographer-mass spectrometer was used with a split injection volume of 5 μL, a transfer port temperature of 260° C., separation through a DB-5,10-m×0.18-mm×0.20-μm column with helium carrier flow at 1 mL/min. The temperature program was 80° C. for 2 minutes, 20° C./minute to 260° C., 260° C. for 2 minutes, and mass ranges were monitored from 70 to 200 mass-to-charge ratio. Quantitations are based on comparisons of IAA peaks to $^{13}$C-IAA standards normalized to fresh weight of original sample.

Example 16

YUCCA6 is Involved in a Trp-Dependent IAA Biosynthesis Pathway

It has been proposed that plants use tryptamine (Trp)-dependent and Trp-independent routes to synthesize auxin (Normanly et al., 1993; Müller and Weiler, 2000; Woodward and Bartel, 2005). To investigate in which pathway YUCCA6 may participate, we tested the resistance of yucca6-1D and yucca6-2D to the toxic Trp analog, 5-methyl-Trp. When yucca6-1D and yucca6-2D were grown in MS medium containing 80 NM 5-methyl-Trp, yucca6-1D and yucca6-2D could survive and grow, whereas wild-type plants could not, indicating that YUCCA6 is involved in Trp-dependent auxin biosynthesis.

It has been reported that maltose-binding protein (MBP):YUCCA1 fusion proteins have catalytic activity to convert tryptamine to N-hydroxyl tryptamine (Zhao et al., 2001). To investigate if YUCCA6 also is involved in oxidation of tryptamine, we tested YUCCA6 activity with MBP:YUCCA6 fusion protein expressed in and purified from bacteria. It is known that FMOs oxidize NADPH by transfer of electrons to oxygen. Expressed YUCCA6 has a $K_m$ of approximately 0.274 mM and a $V_{max}$ of 9.46 Nmol NADPH min$^{-1}$ mg$^{-1}$ using tryptamine as a substrate. The catalytic activity of YUCCA6 for oxidation of tryptamine, together with resistance of yucca6 mutants to 5-methyl-Trp, strongly implies that YUCCA6 has an important function in Trp-dependent auxin biosynthesis.

Example 17

Expression and Purification of MBP:YUCCA6 Fusion Protein

The full-length YUCCA6 ORF was synthesized from Col-0 cDNA by PCR amplification and subcloned into the expression vector pMAL-c2. For PCR, two oligonucleotide primers, designated primer A (5'-CGGAATTCATG-GATTTCTGTTGGAAGAGA-3') (SEQ ID NO:26) and primer B (5'-CCAAGCTTTCAGATTTTTTTTACT-TGCTCGTC-3') (SEQ ID NO:27), were used. The cloning of a YUCCA6 PCR fragment into the EcoRI and HindIII sites of the vector pMAL-c2 allowed the fusion of the YUCCA6 ORF at the 5' end of sequences encoding the MBP and was named MBP:YUCCA6. Competent BL21 *Escherichia coli* cells were transformed with MBP:YUCCA6 plasmid. After inoculation with 20 mL of overnight-grown culture of BL21 containing MBP:YUCCA6, the culture was grown at 37° C. until $A_{600}$ was approximately 0.5. Then, 0.1 mM of isopropyl CD-thiogalactopyranoside was added to the culture to induce expression of recombined protein, and the culture was incubated for an additional 3 h at 28° C. The culture was harvested at 4° C. by centrifugation at 5,000 g for 10 minutes. The bacterial pellet was resuspended in lysis buffer (100 mM potassium phosphate, pH 8.0, 0.1 mM EDTA, 0.5 mM phenylmethylsulfonylfluoride). The mixture was sonicated with a sonicator (550 Sonic Dismembrator; Fisher Scientific) and then centrifuged at 14,000 g for 20 minutes to remove cellular debris. The supernatant was passed through an amylose column that was pre-equilibrated in column buffer (100 mM potassium phosphate, pH 8.0). The amylose column was washed with column buffer. Proteins were released with elution buffer (50 mM potassium phosphate containing 10 mM maltose). MBP was used as a negative control after expression and purification by the same method as MBP:YUCCA6 protein. The protein contents were measured using BIO-RAD Protein Assay (no. 500-0006), and protein was separated by SDS-PAGE.

Example 18

Analysis of Recombinant YUCCA6 Enzyme Activity

The activities of MBP:YUCCA6 and MBP proteins were measured by determining the rates of substrate-dependent NADPH oxidation consumption. Reactions were performed in 1.0 mL of reaction mixture containing 50 mM potassium phosphate, pH 8.0, 0.1 mM NADPH, 0.1 to 0.2 mg recombinant protein, and various concentrations of tryptamine in the sample cuvette and everything except tryptamine in the reference cuvette. The rates of NADPH oxidation caused by addition of tryptamine were monitored at 340 nm for 5 minutes at 22° C. using a UV-visible spectrophotometer (model UV-1601; Shimazu). The change in absorbance per minute was converted to micromoles NADPH consumed per minute using the extinction coefficient 6,220 M$^{-1}$ cm$^{-1}$ for NADPH. $K_m$ and $V_{max}$ values were obtained by regression analysis with Sigma Plot (SPSS).

Example 19

YUCCA6 is Normally Expressed in Roots Cauline Leaves, and Flowers

The transcript levels of YUCCA6 in different organs of wild-type and yucca6 mutant plants were investigated by RT-PCR. In the yucca6-1D plants, the transcript of YUCCA6 was highly expressed in all the tissues tested, including roots and etiolated hypocotyls, where no change in phenotypes was observed. In wild-type plants, the transcript of YUCCA6 was highly expressed in roots but modestly expressed in the cauline leaves and flowers, including bud clusters. This is consistent with the expression profiles of YUCCA6 (At5g25620) provided by AtGenExpress Visualization Tool (Schmid et al., 2005). The YUCCA6 transcript levels indicate that the YUCCA6 gene may be involved normally in auxin-mediated processes, mainly in roots. Overexpression of YUCCA6 in yucca6-1D resulted in increased transcript levels of YUCCA6 in several tissues but not in roots, where YUCCA6 transcript is already very high in the wild type. As mentioned earlier, this may explain the lack of effect of activation of YUCCA6 on root phenotypes. SALK_093708 was identified from the Salk Institute Genome Analysis Laboratory database, and the presence of a T-DNA insertion in the first intron of At5g25620 was confirmed by diagnostic PCR analysis according to the SALK T-DNA verification protocol. Transcript of YUCCA6 was not detected in homozygous SALK_093708 plants under our conditions, suggesting that SALK_093708 is a loss-of-function mutation of YUCCA6. We named SALK_093708 yucca6-3k. Homozygous yucca6-3k plants exhibited visible phenotypes opposite to YUCCA6 overexpression mutants, such as wider rosette leaves and decreased plant height at maturity compared to wild-type plants. However, root morphology of yucca6-3k was not distinctively different from wild-type roots.

Example 20

YUCCA6 Protein is Localized in a Cytoplasmic Compartment

To elucidate subcellular localization of YUCCA6 proteins of the present invention, we constructed plasmids encoding YUCCA6:GFP and YUCCA6:RFP fusion proteins driven by the 35S promoter. YUCCA6:GFP was transiently expressed in *Arabidopsis* protoplasts, and green fluorescent signals were observed by confocal microscopy. To confirm if YUCCA6:GFP fusion protein is functional or not, we analyzed the expression levels of the auxin-responsive GH3 gene (At2g23170). Expression of YUCCA6:GFP promoted expression of GH3, but expression of GFP alone did not increase the transcript level of GH3. This result indicated that YUCCA6:GFP was functional.

Both YUCCA6:GFP and YUCCA6:RFP exhibited largely colocalized patterns of discrete spots of fluorescence. To identify the subcellular compartments where localization of YUCCA6 occurs, YUCCA6:GFP and YUCCA6:RFP were co-expressed with several organelle markers. F1-ATPase-H: RFP was used to identify mitochondria (Jin et al., 2003), rat sialyltransferase:GFP was used to identify the Golgi apparatus (Jin et al., 2001), BiP:RFP was used to identify endoplasmic reticulum compartments (Jin et al., 2001), RFP:SKL was used to identify the peroxisome (Lee, et al., 2002), and chlorophyll autofluorescence was used to mark chloroplasts. YUCCA6:GFP/RFP fusions did not colocalize with any of these subcellular markers. YUCCA6 appears to function in the cytosol or in an unidentified endomembrane compartment.

Subcellular Localization of YUCCA6. To generate Pro$_{35S}$: YUCCA6:GFP and Pro$_{35S}$: YUCCA6:RFP, the full-length YUCCA6 ORF without the stop codon was synthesized with the following primer sets: primer C (5-CTCTAGAATG-GATTTCTGTTGGAAGAGA-3) (SEQ ID NO:28) and primer D (5-CGGATCCAGATTTTTTTTACTTGCTCGT-3) (SEQ ID NO:29) for Pro$_{35S}$:YUCCA6:GFP, and primer C and primer F (5-CGGATCCTCAGATTTTTTTTACTTGCTC-3) (SEQ ID NO:30) for Pro$_{35S}$:YUCCA6:RFP. The PCR products were sub-cloned in frame at the BamHI and XbaI sites of the 326-GFP and 326-RFP expression vectors POSTECH (Pohang, Korea).

All references cited in the present application are incorporated by reference herein to the extent there is no inconsistency with the present disclosure. References cited herein reflect the level of skill in the relevant arts.

REFERENCES

Alonso J M, Stepanova A N, Leisse T J, Kim C J, Chen H, Shinn P, Stevenson D K, Zimmerman J, Barajas P, Cheuk R (2003) Genome-wide insertional mutagenesis of *Arabidopsis thaliana*. Science 301: 653-657

Bak S, Feyereisen R (2001) The involvement of two P450 enzymes, CYP83B1 and CYP83A1, in auxin homeostasis and glucosinolate biosynthesis. Plant Physiol 127: 108-118

Bak S, Nielsen H L, Halkier B A (1998) The presence of CYP79 homologs in glucosinolate-producing plants shows evolutionary conservation of the enzymes in the conversion of amino acid to aldoxime in the biosynthesis of cyanogenic glucosides and glucosinolates. Plant Mol Biol 38: 725-734

Bak S, Tax F E, Feldmann K A, Galbraith D W, Feyereisen R (2001) CYP83B1, a cytochrome P450 at the metabolic branchpoint in auxin and indole glu-cosinolate biosynthesis in *Arabidopsis thaliana*. Plant Cell 13: 101-111

Barlier I, Kowalczyk M, Marchant A, Ljung K, Bhalerao R, Bennett M, Sandberg G, Bellini C (2000) The SUR2 gene of *Arabidopsis thaliana* en-codes the cytochrome P450 CYP83B1, a modulator of auxin homeostasis. Proc Natl Acad Sci USA 97: 14819-14824

Blakeslee J J, Peer W A, Murphy A S (2005) Auxin transport. Curr Opin Plant Biol 8: 1-7

Boerjan W, Cervera M T, Delarue M, Beeckman T, Dewitte W, Bellini C, Caboche M, Van Onckelen H, Van Montagu M, Inze D (1995) superroot, a recessive mutation in *Arabidopsis*, confers auxin overproduction. Plant Cell 7: 1405-1419

Cheng Y, Dai X, Zhao Y (2006) Auxin biosynthesis by the YUCCA flavin monooxygenases controls the formation of floral organs and vascular tissues in *Arabidopsis*. Genes Dev 20: 1790-1799

Clough S J, Bent A F (1998) A simplified method for *agrobacterium*-mediated transformation of *Arabidopsis thaliana*. Plant J 16: 735-743

Davies P J (2004) Plant Hormones: Biosynthesis, Signal Transduction, Action, Ed 3. Kluwer Academic Publishers, Dordrecht, The Netherlands, pp 4-6

Delarue M, Prinsen E, Van Onckelen H, Caboche M, Bellini C (1998) sur2 mutations of *Arabidopsis thaliana* define a new locus involved in the control of auxin homeostasis. Plant J 14: 603-611

Dharmasiri N, Dharmasiri S, Estelle M (2005) The F-box protein TIR1 is an auxin receptor. Nature 435: 441-445

Estelle M, Somerville C (1987) Auxin-resistant mutants of *Arabidopsis thaliana* with an altered morphology. Mol Gen Genet. 206: 200-206

Geisler et al (2005) Cellular efflux of auxin catalyzed by the *Arabidopsis* MDR/PGP transporter AtPGP1. Plant J. 44(2): 179-94

Gong Q, Li P, Ma S, Rupassara S I, Bohnert H J (2005) Salinity stress adaptation competence in the extremophile *Thellungiella halophila* in comparison with its relative *Arabidopsis thaliana*. Plant J 44: 826-839

Hegde P, Qi R, Abernathy K, Gay C, Dharap S, Gaspard R, Hughes J E, Snesrud E, Lee N, Quackenbush J (2000) A concise guide to cDNA microarray analysis. Biotechniques 29: 548-550

Hellman H, Hobbie L, Chapman A, Dharmasiri S, Dharmasiri N, del Pozo C, Reinhardt D, Estelle M (2003) *Arabidopsis* AXR6 encodes CUL1 implicating SCF E3 ligases in auxin regulation of embryogenesis. EMBO J. 22: 3314-3325

Jaakola L, Pirttila A M, Halonen M, Hohtola A (2001) Isolation of high quality RNA from bilberry (*Vaccinium myrtillus* L.) fruit. Mol Biotechnol 19: 201-204

Jefferson R A, Kavanagh T A, Bevan M W (1987) Histochemical localization of C-glucuronidase (GUS) reporter activity in plant tissues. EMBO J. 6: 3901-3907

Jin J B, Bae H, Kim S J, Jin Y H, Goh G H, Kim D H, Lee Y J, Tse Y C, Jiang L, Hwang I (2003) The *Arabidopsis* dynamin-like proteins ADL1C and ADL1 E play a critical role in mitochondrial morphogenesis. Plant Cell 15: 2357-2369

Jin J B, Kim Y A, Kim S J, Lee S H, Kim D H, Cheong G, Hwang 1 (2001) A new dynamin-like protein, ADL6, is involved in trafficking from the trans-Golgi network to the central vacuole in *Arabidopsis*. Plant Cell 13: 1511-1526

Kepinski S, Leyser 0 (2005) The *Arabidopsis* F-box protein TIR1 is an auxin receptor. Nature 435: 446-451

King J J, Stimart D P, Fisher R H, Bleecker A B (1995) A mutation altering auxin homeostasis and plant morphology in *Arabidopsis*. Plant Cell 7: 2023-2037

Lee K H, Kim D H, Lee S W, Kim Z H, Hwang I (2002) In vivo import experiments in protoplasts reveal the importance of the overall context, but not specific amino acid residues of the transit peptide during import into chloroplasts. Mol Cells 14: 388-397

Liu C, Muchhal U S, Uthappa M, Kononowicz A K, Raghothama K G (1998) Tomato phosphate transporter genes are differentially regulated in plant tissues by phosphorus. Plant Physiol 116: 91-99

Liu Y G, Mitsukawa N, Oosumi T, Whittier R F (1995) Efficient isolation and mapping of *Arabidopsis thaliana* T-DNA insert junctions by thermal asymmetric interlaced PCR. Plant J 8: 457-463

Ljung K, Hull A K, Kowalczyk M, Marchant A, Celenza J, Cohen J D, Sandberg G (2001) Biosynthesis, conjugation, catabolism and homeostasis of indole-3-acetic acid in *Arabidopsis thaliana*. Plant Mol Biol 49: 249-272

Ljung K, Hull K A, Celenza J, Yamada M, Estelle M, Normanly J, Sandberg G (2005) Sites and regulation of auxin biosynthesis in *Arabidopsis* roots. Plant Cell 17: 1090-1104

Marsch-Martinez N, Greco R, VanArkel G, Herrera-Estrella L, Pereira A (2002) Activation tagging using the En-I maize transposon system in *Arabidopsis*. Plant Physiol 129: 1544-1556m Mikkelsen M D, Hansen C H, Wittstock U, Halkier B A (2000) Cytochrome P450 CYP79B2 from *Arabidopsis* catalyzes the conversion of tryptophan to indole-3-acetaldoxime, a precursor of indole glucosinolates and indole-3-acetic acid. J Biol Chem 275: 33712-33717

Miura K, Rus A, Sharkhuu A, Yokoi S, Karthikeyan A S, Raghothama K G, Baek D W, Koo Y D, Jin J B, Bressan R A, et al (2005) The *Arabidopsis* SUMO E3 ligase SIZ1 controls phosphate deficiency responses. Proc Natl Acad Sci USA 102: 7760-7765

Miyazaki S, Fredricksen M, Hollis K C, Poroyko V, Shepley D, Galbraith D W, Long S, Bohnert H J (2004) Transcript expression profiles of *Arabidopsis thaliana* grown under controlled conditions and open-air elevated concentrations of $CO_2$ and of $O_3$. Field Crops Res 90: 47-59

Muday G K, DeLong A (2001) Polar auxin transport: controlling where and how much. Trends Plant Sci 6: 535-542

Müller A, Hillebrand H, Weiler E W (1998) Indole-3-acetic acid is synthesized from L-tryptophan in roots of *Arabidopsis thaliana*. Planta 206: 362-369

Müller A, Weiler E W (2000) Indolic constituents and indole-3-acetic acid biosynthesis in the wild-type and a tryptophan auxotroph mutant of *Arabidopsis thaliana*. Planta 211: 855-863

Normanly J, Cohen J D, Fink G R (1993) *Arabidopsis thaliana* auxotrophs reveal a tryptophan-independent biosynthetic pathway for indole-3-acetic acid. Proc Natl Acad Sci USA 90:10355-10359

Romano C P, Cooper M L, Klee H J (1993) Uncoupling auxin and ethylene effects in transgenic tobacco and *Arabidopsis* plants. Plant Cell 5: 181-189

Rus A, Yokoi S, Sharkhuu A, Reddy M, Lee B H, Matsumoto T K, Koiwa H, Zhu J K,

Bressan R A, Hasegawa P M (2001) AtHKT1 is a salt tolerance determinant that controls Na□ entry into plant roots. Proc Natl Acad Sci USA 98: 14150-14155

Saeed A L, Sharov V, White J (2003) TM4: a free, opensource system for microarray data management and analysis. Biotechniques 34: 374-378

Schmid M, Davison T S, Henz S R, Pape U J, Demar M, Vingron M, Scholkopf B, Weigel D, Lohmann J U (2005) A gene expression map of *Arabidopsis thaliana* development. Nat Genet. 37: 501-506

Smolen G, Bender J (2002) *Arabidopsis* cytochrome P450 cyp83B1 mutations activate the tryptophan biosynthetic pathway. Genetics 160: 323-332

Swarup R, Bennett M (2003) Auxin transport: the fountain of life in plants? Dev Cell 5:

Tobeña-Santamaria R, Bliek M, Ljung K, Sandberg G, Mol J N M, Souer E, Koes R (2002) FLOOZY of petunia is a flavin mono-oxygenase-like protein required for the specification of leaf and flower architecture. Genes Dev 16: 753-763

Ulmasov T, Murfett J, Hagen G, Guilfoyle T J (1997) Aux/IAA proteins repress expression of reporter genes containing natural and highly active synthetic auxin response elements. Plant Cell 9: 1963-1971

Woodward A, Bartel B (2005) Auxin: regulation, action, and interaction. Ann Bot (Lond) 95: 707-735

Woodward C, Bemis S M, Hill E J, Sawa S, Koshiba T, Torii K (2005) Interaction of auxin and ERECTA in elaborating *Arabidopsis* inflorescence architecture revealed by the activation tagging of a new member of the YUCCA family putative flavin monooxygenases. Plant Physiol 139: 192-203

Yamamoto Y, Kamiya N, Morinaka Y, Matsuoka M, Sazuka T (2007) Auxin biosynthesis by the YUCCA genes in rice. Plant Physiol 143: 1362-1371

Yang X, Lee S, So J H, Dharmasiri S, Dharmasiri N, Ge L, Gensen C, Hangarter R, Hobbie L, Estelle M (2004) The IAA1 protein is encoded by AXR5 and is a substrate of SCF (TIR1). Plant J 40: 772-782

Zhao Y, Christensen S K, Fankhauser C, Cashman J R, Cohen J D, Weigel D, Chory J (2001) A role for flavin monooxygenase-like enzymes in auxin biosynthesis. Science 291: 306-309

Zhao Y, Hull A K, Gupta N R, Goss K A, Alonso J, Ecker J R, Normanly J, Chory J, Celenza I L (2002) Trp-dependent auxin biosynthesis in *Arabidopsis*: involvement of cytochrome P450s CYP79B2 and CYP79B3. Genes Dev 16:3100-3112

What is claimed is:

1. A method for producing a drought tolerant plant, said method comprising:
   a. stably transforming a plant with an expression vector comprising a nucleotide sequence encoding a flavin-containing monooxygenase having the amino acid sequence of SEQ ID NO: 1;
   b. screening the resulting transformed plant for drought tolerance, and
   c. selecting a stably transformed plant that is more drought tolerant than a non-transformed control plant.

2. The method of claim 1, wherein said plant is *Arabidopisis thaliana*.

3. The method of claim 1, wherein the nucleotide sequence is the sequence of SEQ ID NO: 2.

4. The method of claim 1, wherein the nucleotide sequence is the sequence of SEQ ID NO:3.

5. The method of claim 1, wherein the nucleotide sequence is the sequence of SEQ ID NO:4.

6. A method for producing a plant with delayed senescence, said method comprising:
   a. stably transforming a plant with an expression vector comprising a nucleotide sequence encoding a flavin-containing monooxygenase having the amino acid sequence of SEQ ID NO: 1;
   b. screening the resulting transformed plant for delayed senescence; and
   c. selecting a stably transformed plant that has delayed senescence compared to a non-transformed control plant.

7. The method of claim 6, wherein said plant is *Arabidopisis thaliana*.

8. The method of claim 6, wherein the nucleotide sequence is the sequence of SEQ ID NO:2.

9. The method of claim 6, wherein the nucleotide sequence is the sequence of SEQ ID NO:3.

10. The method of claim 6, wherein the nucleotide sequence is the sequence of SEQ ID NO:4.

* * * * *